(12) United States Patent
Takahashi et al.

(10) Patent No.: US 11,781,115 B2
(45) Date of Patent: Oct. 10, 2023

(54) PRIMARY CULTURE METHOD

(71) Applicants: TOPPAN PRINTING CO., LTD., Tokyo (JP); Japanese Foundation For Cancer Research, Tokyo (JP)

(72) Inventors: Yuki Takahashi, Tokyo (JP); Shiro Kitano, Tokyo (JP); Ryohei Katayama, Tokyo (JP); Satoshi Nagayama, Tokyo (JP)

(73) Assignees: TOPPAN PRINTING CO., LTD., Yo (JP); JAPANESE FOUNDATION FOR CANCER RESEARCH, Tokyo (JP)

( * ) Notice: Subject to any disclaimer, the term of this patent is extended or adjusted under 35 U.S.C. 154(b) by 522 days.

(21) Appl. No.: 16/782,579

(22) Filed: Feb. 5, 2020

(65) Prior Publication Data
US 2020/0172874 A1  Jun. 4, 2020

Related U.S. Application Data

(63) Continuation of application No. PCT/JP2018/030777, filed on Aug. 21, 2018.

(30) Foreign Application Priority Data

Aug. 21, 2017  (JP) ................. 2017-158901

(51) Int. Cl.
*C12N 5/09* (2010.01)

(52) U.S. Cl.
CPC ........ *C12N 5/0693* (2013.01); *C12N 2502/11* (2013.01); *C12N 2502/1323* (2013.01); *C12N 2502/28* (2013.01); *C12N 2509/10* (2013.01); *C12N 2513/00* (2013.01); *C12N 2533/30* (2013.01); *C12N 2533/90* (2013.01)

(58) Field of Classification Search
CPC .............. C12N 5/0693; C12N 2502/11; C12N 2502/1323; C12N 2502/28; C12N 2509/10; C12N 2513/00; C12N 2533/30; C12N 2533/90
See application file for complete search history.

(56) References Cited

U.S. PATENT DOCUMENTS

2004/0241837 A1  12/2004  Nakatsugawa
2015/0282885 A1*  10/2015  King ...................... B33Y 10/00
                                                                  506/14

FOREIGN PATENT DOCUMENTS

| CN | 106867959 A | 6/2017 | |
|---|---|---|---|
| EP | 3187580 A1 * | 7/2017 | ............. C12N 11/02 |
| EP | 3187580 A1 | 7/2017 | |
| JP | 2000-217570 | 8/2000 | |
| JP | 2007-186492 | 7/2007 | |
| JP | 2007-222155 | 9/2007 | |
| JP | 2012-115254 | 6/2012 | |
| JP | 5652809 | 1/2015 | |
| WO | WO 03/039611 | 5/2003 | |
| WO | WO 2015/079759 | 6/2015 | |
| WO | WO 2017/146124 A1 | 8/2017 | |
| WO | WO 2017/183676 A1 | 10/2017 | |
| WO | WO 2017/183677 A1 | 10/2017 | |

OTHER PUBLICATIONS

R. Ian Freshney, "Culture of Tumor Cells." In: Culture of Animal Cell: A Manual of Basic Technique and Specialized Applications. (Hoboken, NJ, John Wiley & Sons, Inc., 2010), pp. 463-479. QH585.2.F74 2010. (Year: 2010).*
Extended European Search Report dated Apr. 29, 2021 in related European Patent Application No. 18847307.8 (10 pages).
Kidambi Srivatsan et al: "Patterned Co-Culture of Primary Hepatocytes and Fibroblasts Using Polyelectrolyte Multilayer Templates", Macromolecular Bioscience, vol. 7, No. 3, Mar. 8, 2007 (Mar. 8, 2007), pp. 344-353, XP055796881, DE; (10 pages).
Brown Daniel D et al: "Developing in vitro models of human ductal carcinoma in situ from primary tissue explants", Breast Cancer Research and Treatment, Springer, NY, US, vol. 153, No. 2, Aug. 18, 2015 (Aug. 18, 2015), XP035539732, pp. 311-321, [retrieved on Aug. 18, 2015] (11 pages).
Degrassi A. et al: "In vitro culture of primary plasmacytomas requires stromal cell feeder layers.", Proceedings of the National Academy of Sciences, vol. 90, No. 5, Mar. 1, 1993 (Mar. 1, 1993), pp. 2060-2064, XP055796897, (5 pages).
International Search Report dated Nov. 20, 2018, in corresponding International Patent Application No. PCT/JP2018/030777.
Takamura et al., "Prediction of Chemotherapeutic Response by Collagen Gel Droplet Embedded Culture-Drug Sensitivity Test in Human Breast Cancers" International Journal of Cancer, 2002, vol. 98, p. 450-455.
Zhang L et al., ROCK Inhibitor Y-27632 Suppresses Dissociation-Induced Apoptosis of Murine Prostate Stem/Progenitor Cells and Increases Their Cloning Efficiency Plos One, 2011, vol. 6, p. 18271.
Nishiguchi et al., "Cell-Cell Crosslinking by Bio-Molecular Recognition of Heparin-based Layer-by-Layer Nanofilms" Macromol Bioscience, 2015, vol. 15(3), p. 312-317.
Office Action dated Mar. 1, 2023 in Chinese Patent Application No. 201880053730.4 (8 pages; 8 pages English translation).

* cited by examiner

*Primary Examiner* — Kara D Johnson

(57) ABSTRACT

A primary culture method in which cells contained in a tissue collected from a living body are primary cultured in vitro, in which the cells in the tissue collected from the living body are seeded and cultured on a top surface of a cell structure containing cells constituting a stroma and composed of a single layer or two or more cell layers laminated in the thickness direction.

15 Claims, 9 Drawing Sheets

Bar: 1000 μm

Bar: 1000 μm

JC052-3-liv (NO STROMA)

Bar: 1000 μm

3D STROMA (NO CANCER CELLS)

Bar: 1000 μm

PRIMARY CULTURE METHOD

CROSS REFERENCE TO RELATED APPLICATIONS

This application is a continuation application based on a PCT Patent Application No. PCT/JP2018/030777, filed Aug. 21, 2018, whose priority is claimed on Japanese Patent Application No. 2017-158901, filed on Aug. 21, 2017, the entire contents of which are hereby incorporated by reference.

BACKGROUND OF THE INVENTION

Field of the Invention

The present invention relates to a method for primary culture of cells in a tissue collected from a living body. In particular, the present invention relates to a method for primary culture of cancer cells derived from a tumor tissue of a cancer patient.

Priority is claimed on Japanese Patent Application No. 2017-158901, filed on Aug. 21, 2017, the entire contents of which are incorporated herein by reference.

Description of Related Art

Conventionally, in cancer research, experiments using cell lines established by subculture under conditions optimized for culture have been the mainstream. However, cancer cell lines that have been maintained and cultured in vitro for many years have changed in nature from the original patient tumor tissue, and there is a possibility that they cannot be said to fully reflect the behavior in vivo. Accordingly, primary culture of cancer cells has been regarded as promising for the development of anticancer drugs with higher accuracy and the selection of optimal treatment for each patient.

For example, Takamura et al. (International Journal of Cancer, 2002, Vol. 98, pp. 450-455) introduces a collagen gel droplet embedded culture-drug sensitivity test (CD-DST) method using primary cultured cells. This test method is a drug sensitivity test in which tissues or cells isolated from a patient are embedded and cultured in a collagen gel for verification. However, a culture method for primary cultured cells can be hardly described as being established, and a low rate of successful culture has been a problem.

As a method for primary culturing of cancer cells from a patient tumor tissue, a method for adding Y-27632 serving as a ROCK inhibitor to a medium in order to inhibit cell death (apoptosis) accompanying cell dispersion (refer to Zhang L et al., PLOS ONE, 2011, vol. 6, p. 18271) and a method in which a cell aggregate of a certain size is obtained while maintaining cell-cell adhesion and grown in suspension culture (refer to Japanese Patent No. 5652809) have been proposed. In these culture methods, a medium in which a serum substitute or various growth factors are added to a serum-free medium for stem cells is used. However, in general, in addition to the serum-free medium for stem cells being expensive, there is a possibility that signaling pathways different from those in the actual living body may be enhanced or suppressed in a growth environment in which a large amount of growth factors have been artificially added. In such an environment, there is a concern that a result different from that in an actual living body may be obtained particularly in a sensitivity test or the like using a molecularly targeted drug.

SUMMARY OF THE INVENTION

Technical Problem

The present invention has an object of providing a method for primary culture of cells in a tissue (biological tissue) collected from a living body using a culture medium used for general cell culture without particularly adding a growth factor or some form of inhibitor.

Solution to Problem

As a result of intensive studies conducted in order to solve the above-mentioned problems, the inventors of the present invention have discovered the following, which has led to the completion of the present invention: that is, when cells in a tissue collected from a living body are cultured outside the cell, the presence of stroma is important at the initial stage of the culture.

[1] A primary culture method according to a first aspect of the present invention is a primary culture method in which cells contained in a tissue collected from a living body are primary cultured in vitro, wherein the cells in the tissue collected from the living body are seeded and cultured on a top surface of a cell structure containing cells constituting a stroma and composed of a single layer or two or more cell layers laminated in the thickness direction.

[2] A fragmented material of the tissue collected from the aforementioned living body, an enzyme-treated product of the tissue collected from the living body, or a cell recovered from the tissue collected from the aforementioned living body may be seeded and cultured on the top surface of the cell structure.

[3] The cell structure may include one or more members selected from the group consisting of fibroblasts, pericytes, endothelial cells, and immune cells as the cells constituting the stroma.

[4] The endothelial cells may be one or more members selected from the group consisting of vascular endothelial cells and lymphatic endothelial cells.

[5] The cell structure may include a vascular network structure.

[6] The thickness of the cell structure may be 5 μm or more.

[7] The thickness of the cell structure may be 150 μm or more.

[8] The tissue collected from the living body may contain a tumor tissue.

[9] After the tissue collected from the living body is fragmented, cancer cells are sorted from the obtained fragmented material, and the sorted cancer cells may be seeded and cultured on the top surface of the cell structure.

[10] When sorting the cancer cells from the fragmented material, the cancer cells may be sorted by one or more techniques selected from the group consisting of flow cytometry, magnetic separation, dielectrophoresis, size fractionation, and density gradient fractionation.

[11] The cell structure may be constructed by: a step (a) of obtaining a mixture by mixing cells including at least cells constituting a stroma, a strong polyelectrolyte, and an extracellular matrix component in a cationic buffer solution; a step (b) of seeding the mixture obtained by the aforementioned step (a) in a cell culture vessel; and a step (c) of obtaining a cell structure in which cells including at least cells constituting the stroma are laminated in multiple layers in the cell culture vessel after the step (b).

[12] A primary cultured cell-containing cell structure according to a second aspect of the present invention includes cells constituting a stroma, and a cell layer formed from cells contained in a tissue collected from a living body on a top surface of a stromal cell layer in which a single layer or two or more cell layers are laminated in the thickness direction.

Advantageous Effects of Invention

In the primary culture method according to the above aspect of the present invention, since the cells in the biological tissue are cultured on the top surface of the cell structure imitating the stroma, even without using a large amount of growth factors or special inhibitors as in the conventional primary culture, primary culture can be performed with a high success rate even when a general culture medium commonly used for culturing cell lines is used.

DETAILED DESCRIPTION OF THE INVENTION

Figure 1:
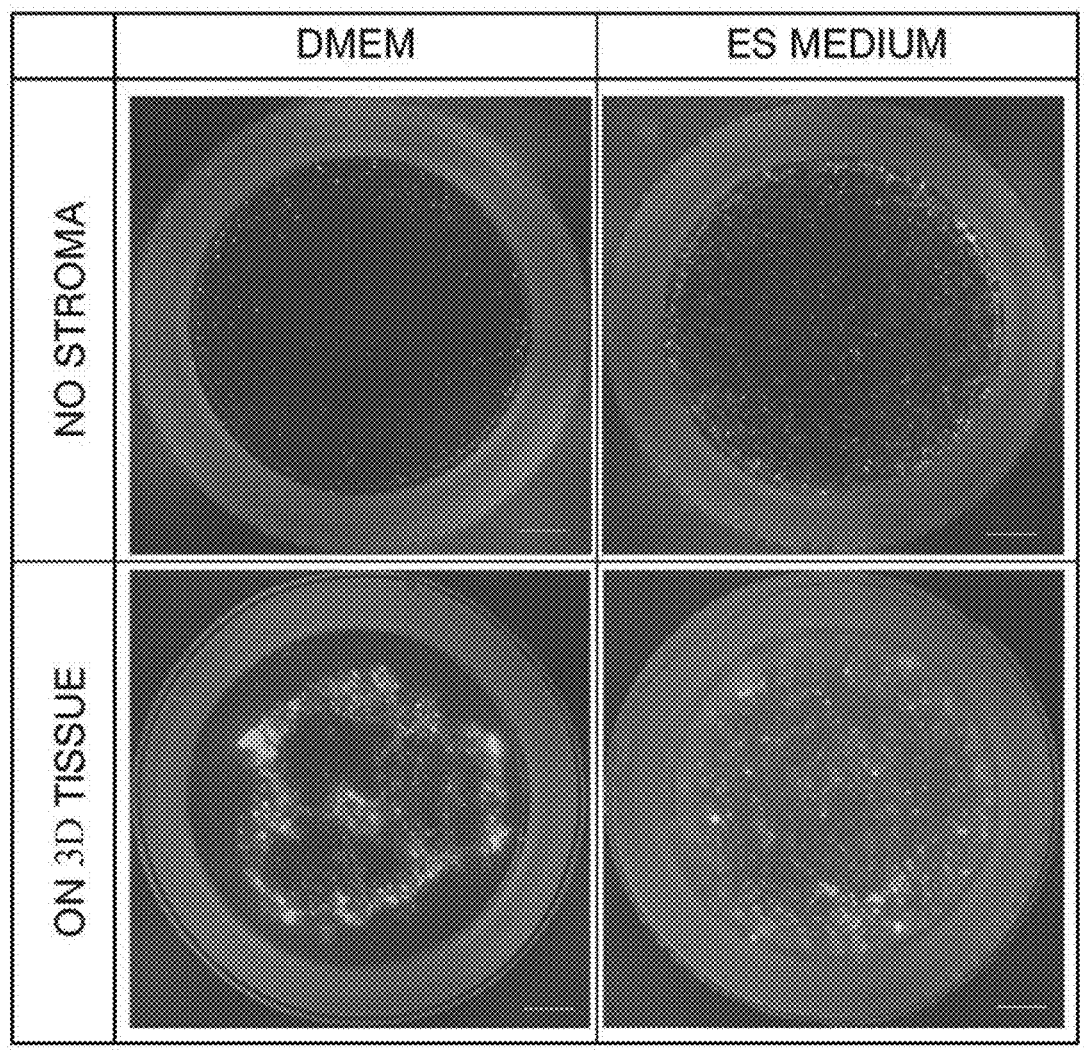
FIG. 1 shows fluorescence images of a cancer cell line JC004 labeled with PKH after culturing for 2 weeks in Example 1.

A primary culture method according to an embodiment of the present invention is a culture method for in vitro primary culture of cells contained in a tissue collected from a living body, and cells in a living tissue are seeded and cultured on the top surface of a cell structure containing cells constituting the stroma (stromal cells) and composed of a single layer or two or more cell layers laminated in the thickness direction. The cell structure used in the present embodiment is a structure that includes stromal cells and imitates a stromal tissue. By culturing cells in a living tissue on the top surface of a cell structure that imitates the stroma rather than the surface of a normal culture substrate, primary culture can be performed with a high success rate even when a general culture medium commonly used for culturing cell lines is used.

In the primary culture method according to the present embodiment, primary culture can be performed on the top surface of a cell structure simulating a stromal tissue without using excessive growth factors or artificial inhibitors as a culture medium. As a result, a primary cultured cell-containing cell structure is obtained, which includes cells constituting a stroma, and a cell layer formed from cells contained in a tissue collected from a living body on a top surface of a stromal cell layer in which a single layer or two or more cell layers are laminated in the thickness direction. In other words, the primary culture (primary cultured cell-containing cell structure) obtained by the present embodiment is a culture obtained in an environment closer to that in the living body. For this reason, the primary culture obtained by the present embodiment is very useful as a sample for performing a cell-based assay closer to that in the living body.

<Cell Structure>

The cell structure used in the present embodiment (hereinafter sometimes referred to as "cell structure according to the present embodiment") includes at least stromal cells and is a single layer or two or more cell layers laminated in the thickness direction. By constructing stromal cells three-dimensionally, a cell structure imitating a stromal tissue can be constructed. It should be noted that in the present embodiment and the present specification, the term "cell structure" means a planar or three-dimensional cell aggregate including at least a stromal cell, and the phrase "thickness of cell structure" means a length of the structure in the gravity direction. The gravity direction is a direction in which gravity is applied and is also referred to as a thickness direction. The term "cell layer" means a layer composed of a group of cells and stroma that exist in a direction perpendicular to the thickness direction and in which cell nuclei do not overlap in the thickness direction.

Cells such as stromal cells constituting the cell structure according to the present embodiment are not particularly limited, and may be cells collected from an animal, cells obtained by culturing cells collected from an animal, cells obtained by subjecting cells collected from an animal to various treatments, or a cultured cell line. Further, commercially available cells may be used, or patient-derived cells may be used. In the case of cells collected from an animal, the sampling site is not particularly limited, and may be somatic cells derived from the bone, muscle, viscus, nerve, brain, bone, skin, blood and the like, may be germ cells, or may be embryonic stem cells (ES cells). Further, the biological species from which the cells constituting the cell structure according to the present embodiment are derived is not particularly limited, and for example, cells derived from animals such as humans, monkeys, dogs, cats, rabbits, pigs, cows, mice, rats, and the like can be used. The cells obtained by culturing cells collected from an animal may be primary cultured cells or subcultured cells. Further, examples of the cells that have been subjected to various treatments include induced pluripotent stem cells (iPS cells) and cells after induced differentiation. Moreover, the cell structure according to the present embodiment may be composed only of cells derived from the same biological species, or may be composed of cells derived from a plurality of biological species.

Examples of stromal cells that construct the cell structure according to the present embodiment include endothelial cells, fibroblasts, pericytes, immune cells, nerve cells, mast cells, epithelial cells, cardiac muscle cells, liver cells, islet cells, tissue stem cells and smooth muscle cells. Immune cells are cells involved in immunity. Specific examples thereof include lymphocytes, macrophages and dendritic cells. Examples of lymphocytes include T cells, B cells, NK cells and plasma cells. The stromal cells contained in the cell structure according to the present embodiment may be one type or two or more types. The stromal cells contained in the cell structure according to the present embodiment preferably include at least one selected from the group consisting of fibroblasts, pericytes, endothelial cells, and immune cells.

The number of stromal cells in the cell structure according to the present embodiment is not particularly limited, but since a cell structure that more closely imitates the stromal tissue can be formed, the abundance ratio (cell number ratio) of stromal cells with respect to all the cells constituting the cell structure according to the present embodiment is preferably 30% or more, more preferably 50% or more, still more preferably 70% or more, and even more preferably 80% or more.

The vascular network structure and the lymphatic network structure are considered to be important for the cell structure according to the present embodiment to exhibit functions similar to those of the stromal tissue in the living body. For this reason, the cell structure according to the present embodiment is preferably a cell structure having a vascular network structure. That is, the cell structure according to the present embodiment is preferably a cell structure in which a vascular network structure such as a lymphatic vessel and/or a blood vessel is three-dimensionally constructed, in a cell laminate in which vessels are not formed, to produce a tissue even closer to that in the living body. The vascular network structure may be formed only inside the cell structure, or may be formed so that at least a part of the vascular network structure is exposed on the upper surface or the bottom surface of the cell structure. Further, the vascular network structure may be constructed in the entire cell structure, or may be formed only in a specific cell layer. It should be noted that in the present embodiment and the present specification, the term "vascular network structure" refers to a net-like structure such as a vascular network or a lymphatic network in a living tissue.

The vascular network structure can be formed by including endothelial cells constituting vessels as stromal cells. The endothelial cells included in the cell structure according to the present embodiment may be vascular endothelial cells or lymphatic endothelial cells. Further, the endothelial cells included in the cell structure according to the present embodiment may include both vascular endothelial cells and lymphatic endothelial cells.

When the cell structure according to the present embodiment has a vascular network structure, cells other than the endothelial cells in the cell structure are preferably cells constituting a tissue surrounding the vessel in the living body since a vascular network in which the endothelial cells retain their original functions and shapes can be easily formed. Since it is possible to more closely approximate the stromal tissue in the living body and the environment in the vicinity of the stromal tissue in the living body, the cells other than the endothelial cells are more preferably cells containing at least fibroblasts, and still more preferably cells containing vascular endothelial cells and fibroblasts, cells containing lymphatic endothelial cells and fibroblasts, or cells containing vascular endothelial cells and lymphatic endothelial cells and fibroblasts. It should be noted that the cells other than the endothelial cells included in the cell structure may be cells derived from the same biological species as that of the endothelial cells, or may be cells derived from different biological species.

The number of endothelial cells in the cell structure according to the present embodiment is not particularly limited as long as it is a sufficient number to form a vascular network structure, and can be appropriately determined in consideration of the size of the cell structure, the cell types of endothelial cells and cells other than endothelial cells, and the like. For example, a cell structure in which a vascular network structure is formed can be prepared by setting the abundance ratio (cell number ratio) of endothelial cells to the total cells constituting the cell structure according to the present embodiment to 0.1% or more. When fibroblasts are used as the cells other than endothelial cells, the number of endothelial cells in the cell structure according to the present embodiment is preferably 0.1% or more, and more preferably 0.1 to 5.0%, of the number of fibroblasts. When both vascular endothelial cells and lymphatic endothelial cells are included as endothelial cells, the total number of vascular endothelial cells and lymphatic endothelial cells is preferably 0.1% or more, and more preferably 0.1 to 5.0%, of the number of fibroblasts.

In particular, when the primary culture obtained by the primary culture method according to the present embodiment is used for a cell-based assay such as a drug sensitivity test, the cell structure to be used is preferably a structure that is even closer to the stroma in vivo. For this reason, the cell structure is preferably a cell structure in which a vascular network structure is formed, and more preferably a cell structure in which a vascular network structure is formed and fibroblasts are included.

Moreover, in order to meet the demand for obtaining more cancer cells, it is preferable to have a vascular network structure.

The size and shape of the cell structure according to the present embodiment are not particularly limited. Since a cell structure in a state closer to that of the stromal tissue in a living body can be formed and primary culture in an environment closer to the living body can be expected, the thickness of the cell structure is preferably 5 μm or more, more preferably 30 μm or more, still more preferably 100 μm or more, and even more preferably 150 μm or more. Further, the thickness of the cell structure is preferably 500 μm or less, more preferably 400 μm or less, and still more preferably 200 μm or less. The number of cell layers in the cell structure according to the present embodiment is preferably about 1 to 60 layers, more preferably about 2 to 60 layers, still more preferably about 5 to 60 layers, and even more preferably about 5 to 20 layers.

It should be noted that when the cell structure has a three-dimensional structure in which two or more cell layers are laminated, the number of cell layers constituting the cell structure is measured by dividing the total number of cells constituting the three-dimensional structure by the number of cells per layer (the number of cells necessary to constitute one layer). The number of cells per layer can be examined by culturing cells in advance on a flat surface so as to be confluent in a cell culture vessel used when constituting the cell structure. More specifically, the number of cell layers in a cell structure formed in a certain cell culture vessel can be calculated by measuring the total number of cells constituting the cell structure and dividing it by the number of cells per layer in the cell culture vessel.

In general, the cell structure according to the present embodiment is constructed in a cell culture vessel. The cell culture vessel is not particularly limited as long as the cell structure can be constructed and the constructed cell structure can be cultured. Specific examples of the cell culture vessel include dishes, cell culture inserts (for example, Transwell (registered trademark) insert, Netwell (registered trademark) inserts, Falcon (registered trademark) cell culture inserts, Millicell (registered trademark) cell culture inserts and the like), tubes, flasks, bottles and plates. In the construction of the cell structure according to the present embodiment, since the constructed cell structure can be used as it is for the primary culture, dishes or various cell culture inserts are preferable.

The cell structure according to the present embodiment may be a structure formed from a single layer or multiple cell layers containing stromal cells, and the construction method of the cell structure is not particularly limited. For example, it may be a construction method for constructing one layer at a time and sequentially laminating it, a method for constructing two or more cell layers at a time, or a method for constructing multiple cell layers by suitably combining both of the construction methods.

In addition, the cell structure according to the present embodiment may be a multilayer structure in which the cell types constituting each cell layer are different for each layer, or the cell types constituting each cell layer may be the same cell type in all layers of the structure. For example, it may be a construction method in which a layer is formed for each cell type, and the cell layers are sequentially laminated, or a method in which a cell mixture solution obtained by mixing a plurality of types of cells is prepared in advance, and a cell structure having a multilayer structure is constructed at a time from the cell mixture solution.

As a construction method for constructing one layer at a time and sequentially laminating it, for example, a method described in Japanese Patent No. 4919464, that is, a method of laminating cell layers continuously by alternately repeating a step of forming a cell layer, and a step of bringing the formed cell layer into contact with a solution containing an extracellular matrix (ECM) component can be mentioned. For example, when performing this method, a cell structure in which a vascular network structure is formed throughout the entire structure can be constructed by preparing a cell mixture in which all cells constituting the cell structure are mixed in advance, and forming each cell layer with this cell mixture. Further, by forming each cell layer for each cell type, a cell structure in which a vascular network structure is formed only in a layer formed from endothelial cells can be constructed.

Examples of the method for constructing two or more cell layers at a time include the method described in Japanese Patent No. 5850419. This method is a method for constructing a cell structure formed from multiple cell layers by coating the entire cell surface in advance with a polymer containing an arginine-glycine-aspartic acid (RGD) sequence to which integrin binds and a polymer interacting with the polymer containing the RGD sequence, storing the coated cells coated with the adhesive film in a cell culture vessel and then accumulating the coated cells by centrifugation or the like. For example, when performing this method, a cell mixture obtained by mixing all cells constituting the cell structure is prepared in advance, and coated cells prepared by adding an adhesive component to the cell mixture are used. This enables the construction of a cell structure in which the cell composition is uniform throughout the entire structure by a single centrifugation process.

The cell structure according to the present embodiment can also be constructed by a method including the following steps (a) to (c):

Step (a): a step (a) of obtaining a mixture by mixing cells and an extracellular matrix component in a cationic buffer solution;

Step (b): a step (b) of seeding the mixture obtained in the step (a) in a cell culture vessel; and Step (c): a step (c) of obtaining a cell structure in which cells are laminated in multiple layers in the cell culture vessel after the step (b).

In the step (a), by mixing cells with a buffer solution containing a cationic material (cationic buffer solution) and an extracellular matrix component and forming a cell aggregate from the cell mixture, it is possible to obtain a three-dimensional cell tissue in which the number of large voids inside is small. Further, since the obtained three-dimensional cell tissue is relatively stable, it can be cultured for at least several days, and the tissue is unlikely to collapse even when the culture medium is replaced. Moreover, in the present embodiment, the step (b) may include precipitating, in a cell culture vessel, the cell mixture seeded in the cell culture vessel. In precipitation of the cell mixture, cells may be actively precipitated by centrifugation or the like, or may be spontaneously precipitated.

In the step (a), it is preferable to further mix the cells with a strong polyelectrolyte. When the cells are mixed with a cationic material, a strong polyelectrolyte, and an extracellular matrix component, a thick three-dimensional cell tissue having a small number of voids can be obtained even when the cells are spontaneously precipitated, without requiring a process such as centrifugal separation for actively gathering the cells in step (b).

Examples of the cationic buffer solution include tris-hydrochloric acid buffers, tris-maleic acid buffers, bis-tris buffers, and HEPES. The concentration and pH of the cationic material (for example, tris in a tris-hydrochloric acid buffer solution) in the cationic buffer solution are not particularly limited as long as they do not adversely affect the cell growth and the construction of the cell structure. For example, the concentration of the cationic material in the cationic buffer solution can be set to 10 to 100 mM, preferably 40 to 70 mM, and more preferably 50 mM. Further, the pH of the cationic buffer solution can be set to 6.0 to 8.0, preferably 6.8 to 7.8, and more preferably 7.2 to 7.6.

Examples of the strong polyelectrolyte include glycosaminoglycans such as heparin, chondroitin sulfate (for example, chondroitin 4-sulfate, chondroitin 6-sulfate), heparan sulfate, dermatan sulfate, keratan sulfate, and hyaluronic acid; dextran sulfate, rhamnan sulfate, fucoidan, carrageenan, polystyrene sulfonic acid, polyacrylamide-2-methylpropane sulfonic acid, and polyacrylic acid, or derivatives thereof, but are not limited thereto. In the mixture prepared in the step (a), only one type of strong polyelectrolyte may be mixed, or two or more types thereof may be combined and mixed. In the construction of the cell structure according to the present embodiment, the strong polyelectrolyte is preferably a glycosaminoglycan. Further, it is more preferable to use at least one of heparin, dextran sulfate, chondroitin sulfate, and dermatan sulfate. The strong polyelectrolyte used in the present embodiment is still more preferably heparin. The amount of the strong polyelectrolyte mixed with the cationic buffer solution is not particularly limited as long as it does not adversely affect the cell growth and the construction of the cell structure.

For example, the concentration of the strong polyelectrolyte in the cationic buffer solution can be set to more than 0 mg/mL (higher than 0 mg/mL) and less than 1.0 mg/mL, preferably 0.025 to 0.1 mg/mL, and more preferably 0.05 to 0.1 mg/mL. Further, in the present embodiment, the cell structure can also be constructed by preparing the above mixture without mixing the strong polyelectrolyte described above.

Examples of the extracellular matrix component include collagen, laminin, fibronectin, vitronectin, elastin, tenascin, entactin, fibrillin, proteoglycan, or modified forms or variants thereof. Examples of proteoglycans include chondroitin sulfate proteoglycan, heparan sulfate proteoglycan, keratan sulfate proteoglycan and dermatan sulfate proteoglycan. In the mixture prepared in the step (a), only one type of extracellular matrix component may be mixed, or two or more types thereof may be combined and mixed. In the construction of the cell structure according to the present embodiment, it is preferable to use collagen, laminin, or fibronectin, and it is more preferable to use collagen. Modified forms and variants of the extracellular matrix components mentioned above may also be used, as long as they do not adversely affect the cell growth and the formation of the cell structure. The amount of the extracellular matrix component mixed with the cationic buffer solution is not particularly limited as long as it does not adversely affect the cell growth and the construction of the cell structure. For example, the concentration of the extracellular matrix component in the cationic buffer solution can be set to more than 0 mg/mL (higher than 0 mg/mL) and less than 1.0 mg/mL, preferably 0.025 to 0.1 mg/mL, and more preferably 0.05 to 0.1 mg/mL.

The mixing ratio of the strong polyelectrolyte and the extracellular matrix component mixed in the cationic buffer solution is 1:2 to 2:1. In the construction of the cell structure according to the present embodiment, the mixing ratio of the strong polyelectrolyte and the extracellular matrix component is preferably 1:1.5 to 1.5:1, and more preferably 1:1.

A cell structure having a sufficient thickness can be constructed by repeating steps (a) to (c); more specifically, as step (b), the mixture prepared in step (a) is seeded on the cell structure obtained in step (c), and step (c) is then performed. The cell composition of the mixture newly seeded on the cell structure obtained in step (c) may be the same as or different from the cell composition constituting the already constructed cell structure.

When the steps (a) to (c) are repeated, the obtained cell structure may be cultured after the step (c) and before the step (b). The culture conditions such as the composition of the culture medium used for the culture, the culture temperature, the culture time, and the atmospheric composition during the culture are those suitable for culturing the cells constituting the cell structure. Examples of the culture medium include D-MEM, E-MEM, MEMα, RPMI-1640 and Ham's F-12.

After step (a), it is also possible to perform the following steps and then proceed to step (b): i.e., (a'-1) a step of removing a liquid portion from the obtained mixture to obtain a cell aggregate; and (a'-2) a step of suspending the cell aggregate in a solution. Although a desired tissue body can be obtained by carrying out the steps (a) to (c) described above, a more uniform tissue body can be obtained by carrying out steps (a'-1) and (a'-2) after step (a), and then carrying out step (b).

Further, after the step (a), the following step (b '-1) and step (b'-2) may be performed instead of the aforementioned step (b). A more uniform tissue body can also be obtained by carrying out the step (b'-1) and the step (b'-2). The step (b'-2) may also include precipitating, in a cell culture vessel, the cell mixture seeded in the cell culture vessel, as in the step (b). In precipitation of the cell mixture, cells may be actively precipitated by centrifugation or the like, or may be spontaneously precipitated. In the present embodiment and the present specification, the term "cell viscous body" refers to a gel-like cell aggregate as described in Nishiguchi et al., Macromol Bioscience, 2015, vol. 15.

Step (b'-1): a step of seeding the mixture obtained in step (a) in a cell culture vessel, and then removing a liquid component from the mixture to obtain a cell viscous body; and Step (b'-2): a step of suspending the cell viscous body in a solvent in the cell culture vessel.

The solvent for preparing a cell suspension is not particularly limited as long as it is a solvent that is not toxic to cells and does not impair the growth properties or function, and water, buffer solutions, cell culture media, and the like can be used. Examples of the buffer solution include phosphate buffered saline (PBS), HEPES and Hanks' buffers. Examples of the culture medium include D-MEM, E-MEM, MEMα, RPMI-1640 and Ham's F-12. When a cell culture medium is used as a solvent for preparing a cell suspension, the cells can be cultured without removing the liquid component in step (c) described later.

The following step (c') may be performed in place of step (c).

Step (c'): a step of forming a cell layer on the substrate.

In step (c) and step (c'), the liquid component may be removed from the seeded mixture. The method for removing the liquid component in the step (c) and the step (c') is not particularly limited as long as it does not adversely affect the cell growth and the construction of the cell structure, and can be appropriately performed by a method known to those skilled in the art as a method for removing a liquid component from a suspension of a liquid component and a solid component. Examples of the method include suction, centrifugation, magnetic separation, or filtration. For example, when a cell culture insert is used as a cell culture vessel, the liquid component can be removed by suction since the cell mixture is precipitated by subjecting the cell culture insert in which the mixture is seeded to a centrifugation treatment at 10° C. and 400×g for 1 minute.

<Cells Contained in Biological Tissue>

The cells cultured in the present embodiment are cells contained in a biological tissue. In the primary culture method according to the present embodiment, a plurality of types of cells contained in a biological tissue may be primary cultured at the same time, or only specific types of cells may be isolated from among the cells contained in the biological tissue and primary cultured.

The biological tissue from which the cells to be cultured in the present embodiment are derived may be a tissue collected from any species of animals. For example, biological tissues collected from animals such as humans, monkeys, dogs, cats, rabbits, pigs, cows, mice and rats can be used.

The biological tissue from which the cells to be cultured in the present embodiment are derived may be a solid tissue or a liquid tissue. Examples of the solid tissue include those obtained by surgically excising and collecting epithelial tissues, connective tissues, muscle tissues, nervous tissues, stromal tissues, and mucosal tissues. Examples of the liquid tissue include body fluids such as blood, lymph, pleural effusions, ascitic fluids, cerebrospinal fluids, tears, saliva, and urine.

These tissues can be removed with a scalpel, laser or the like in surgery, endoscopy or the like, or collected with a syringe, swab or the like. As the human biological tissue, for example, a tissue collected for clinical examination can be used.

The cells cultured in the present embodiment may be a biological tissue derived from a normal tissue or may have some malfunction such as a diseased tissue. For example, by the primary culture method according to the present embodiment, cancer cells contained in a tumor tissue collected from a cancer patient can be primary cultured efficiently. It should be noted that a cancer cell is a cell derived from a somatic cell which has acquired unlimited proliferative capacity. In the primary culture method according to the present embodiment, cancer cells may be primary cultured together with cells other than the cancer cells contained in a tumor tissue collected from a cancer patient, or only the cancer cells may be isolated and primary cultured.

Disease-related cells collected from patients suffering from various diseases such as cancer cells collected from cancer patients can be primary cultured at a high success rate by the primary culture method according to the present embodiment, and the obtained primary cultures of disease-related cells are particularly suitable for cell-based assays. Moreover, the primary culture method according to the present embodiment is also useful for constructing a culture strain of disease-related cells collected from a patient. For example, by primary culturing the cells contained in a patient tumor tissue by the primary culture method according to the present embodiment, patient-derived cancer cell lines reflecting the characteristics of the original patient tumor such as the proliferative capacity rather than those of the normal cell line can be established efficiently.

Examples of cancers from which the cancer cells that are primary cultured in the present embodiment are derived include breast cancer (for example, invasive ductal carcinoma, ductal carcinoma in situ, inflammatory breast cancer and the like), prostate cancer (for example, hormone-dependent prostate cancer, hormone-independent prostate cancer and the like), pancreatic cancer (for example, pancreatic duct cancer and the like), stomach cancer (for example, papillary adenocarcinoma, mucinous adenocarcinoma, adenosquamous carcinoma and the like), lung cancer (for example, non-small cell lung cancer, small cell lung cancer, malignant mesothelioma and the like), colon cancer (for example, gastrointestinal stromal tumor and the like), rectal cancer (for example, gastrointestinal stromal tumor and the like), colorectal cancer (for example, familial colorectal cancer, hereditary non-polyposis colorectal cancer, gastrointestinal stromal tumor and the like), small intestine cancer (for example, non-Hodgkin lymphoma, gastrointestinal stromal tumor and the like), esophageal cancer, duodenal cancer, tongue cancer, pharyngeal cancer (for example, nasopharyngeal cancer, oropharyngeal cancer, hypopharyngeal cancer and the like), head and neck cancer, salivary gland cancer, brain tumor (for example, pineal astrocytoma, pilocytic astrocytoma, diffuse astrocytoma, anaplastic astrocytoma and the like), schwannoma, liver cancer (for example, primary liver cancer, extrahepatic bile duct cancer and the like), renal cancer (for example, renal cell cancer, transitional cell carcinoma of the renal pelvis and ureter, and the like), gallbladder cancer, bile duct cancer, pancreatic cancer, hepatoma, endometrial cancer, cervical cancer, ovarian cancer (for example, epithelial ovarian cancer, extragonadal germ cell tumor, ovarian germ cell tumor, ovarian low malignant potential tumor and the like), bladder cancer, urethral cancer, skin cancer (for example, intraocular (ocular) melanoma, Merkel cell carcinoma and the like), hemangioma, malignant lymphoma (for example, reticulosarcoma, lymphosarcoma, Hodgkin disease and the like), melanoma (malignant melanoma), thyroid cancer (for example, medullary thyroid cancer and the like), parathyroid cancer, nasal cavity cancer, paranasal sinus cancer, bone tumor (for example, osteosarcoma, Ewing tumor, uterine sarcoma, soft tissue sarcoma and the like), metastatic medulloblastoma, angiofibroma, dermatofibrosarcoma protuberans, retinal sarcoma, penile cancer, testicular tumor, pediatric solid cancer (for example, Wilms tumor, pediatric renal tumor and the like), Kaposi sarcoma, Kaposi sarcoma caused by AIDS, maxillary sinus tumor, fibrous histiocytoma, leiomyosarcoma, rhabdomyosarcoma, chronic myeloproliferative disorders, leukemia (for example, acute myelogenous leukemia, acute lymphoblastic leukemia and the like) and the like, but are not limited thereto.

<Primary Culture>

In the primary culture method according to the present embodiment, cells in a biological tissue are seeded and cultured on the top surface of the cell structure according to the present embodiment. More specifically, the cells in the biological tissue are added into the culture solution of the cell structure according to the present embodiment. As a result, the cells in the biological tissue adhere to the top surface of the cell structure, and the cells in the biological tissue are cultured in a state of being adhered to the top surface of the cell structure.

The culture medium used for the culture may be a medium containing a growth factor, a ROCK inhibitor or the like, such as a culture medium generally used in primary culture like StemPro medium, but it is preferably a general culture medium that is widely used for the culture of cell lines.

Examples of the general culture media widely used for culturing cell lines include D-MEM, E-MEM, MEMα, RPMI-1640, Ham's F-12, and these media supplemented with a serum such as calf serum (CS), fetal bovine serum (FBS), and fetal horse serum (HBS) to a concentration of about 1 to 10% by volume.

Further, other culture conditions can be appropriately set in the same manner as general culture conditions of animal cells. For example, the culture temperature is preferably about 30 to 40° C., and most preferably 37° C. Moreover, the $CO_2$ concentration is preferably about 1 to 10% by volume, and most preferably about 5% by volume. In addition, it is also possible to culture in an environment in which the $O_2$ concentration is controlled to be lower than that of the atmospheric air.

When the biological tissue is a solid tissue, it is preferably fragmented in advance so that the cells inside can efficiently adhere to the top surface of the cell structure to start the culture. A mechanical technique using scissors, knives, scalpels, tweezers, and the like is preferably used for fragmenting a biological tissue, but is not particularly limited thereto. The biological tissue is preferably fragmented to a size of, for example, about 5 mm or less, since the cells inside can be taken out more efficiently.

The fragmented biological tissue can be used as it is for primary culture, but it is also preferable to perform an enzyme treatment. Since the cells present inside the fragmented material are exposed on the surface more easily by the enzyme treatment, when this enzyme-treated product is added to the culture medium of the cell structure, they easily adhere to the top surface. The enzyme treatment may be performed when the biological tissue is a liquid tissue. There are also cases where it is difficult for cells contained in a biological tissue to adhere to the top surface of the cell structure only by simple addition of the biological tissue to the culture medium of the cell structure, like the case where the viscosity is high. Such biological tissues are preferably subjected to an enzyme treatment in advance.

The enzyme used for the enzyme treatment of the biological tissue or the fragmented material thereof is not particularly limited, but enzymes that degrade proteins, saccharides, lipids, nucleic acids and the like are preferably used. The enzyme used for the enzyme treatment of the fragmented material of the biological tissue may be one type or two or more types. In the present embodiment, it is preferable to use one or more enzymes selected from the group consisting of trypsin, collagenase, dispase, elastase, papain, and hyaluronidase, it is more preferable to use collagenase or two or more enzymes including collagenase, and it is still more preferable to use collagenase and dispase together with other enzymes as necessary. It should be noted that the enzyme to be used is not particularly limited as long as it is an enzyme having a target enzyme activity, and may be an enzyme derived from any biological species, or may be an artificial enzyme obtained by modifying a naturally occurring enzyme. Further, it may be an enzyme extracted and purified from various cells, or may be a chemically synthesized enzyme.

In the fragmentation treatment or enzyme treatment of the biological tissue, DNase I may be used in combination to prevent cells from clumping together due to the influence of DNA released from cells lysed during the fragmentation treatment or enzyme treatment. The DNase I to be used is not particularly limited as long as it is an enzyme having DNase I activity. Examples of commercially available enzyme mixes that contain a degrading enzyme of biological components such as proteins and DNase I include Liberase Blendzyme 1 (registered trademark) (manufactured by Roche Diagnostics) and Tumor Dissociation Kit (manufactured by Miltenyi Biotec).

The treatment temperature for the enzyme treatment may be any conditions as long as the enzyme to be used can exhibit enzyme activity, but is preferably 30 to 40° C., and more preferably 37° C., since the adverse effects on the cells in the fragmented material of the biological tissue can be suppressed. Further, the treatment time for the enzyme treatment is not particularly limited, and can be set to, for example, 10 to 90 minutes, and preferably 30 to 60 minutes.

It is preferable to count the number of cells in the enzyme-treated product of the biological tissue before seeding it onto the top surface of the cell structure according to the present embodiment, and in particular, it is preferable to count the number of living cells. The number of cells and the number of living cells can be counted by a conventional method. For example, the number of living cells can be counted by a staining method using trypan blue, or the like.

The fragmented material of the biological tissue may be washed with a buffer solution or a culture medium prior to the enzyme treatment. As the buffer solution used for washing, phosphate buffers, acetate buffers, citrate buffers, borate buffers, tartrate buffers, tris buffers, PBS, and the like can be used. Further, an antibiotic can also be added into the buffer solution or culture medium used for washing. It is particularly preferable to wash the tissue can be washed with PBS containing penicillin G (200 U/mL), streptomycin sulfate (200 μg/mL), and amphotericin B (0.5 μg/mL). The number of washing treatments can be appropriately determined depending on the origin of the collected biological tissue, but 3 to 8 times is preferable. Moreover, washing using a buffer solution or a culture medium may be performed only after the enzyme treatment, or before and after the enzyme treatment.

When only specific cells in a biological tissue are cultured on the top surface of the cell structure, only the cells of a target cell type are sorted from the biological tissue or the enzyme-treated product of the biological tissue, and the sorted cells are then added to the culture medium of the cell structure. For example, after sorting cancer cells from an enzyme-treated product of a tumor tissue, only the cancer cells are added to the culture medium of the cell structure.

A method for sorting a specific cell from a biological tissue or an enzyme-treated product of the biological tissue is not particularly limited, and can be appropriately selected from various methods generally used for cell sorting. For example, specific cells can be sorted by one or more techniques selected from the group consisting of flow cytometry, magnetic separation, dielectrophoresis, size fractionation, and density gradient fractionation.

When sorting only cancer cells from a biological tissue derived from a cancer patient or an enzyme-treated product of the biological tissue and culturing the sorted cancer cells on the top surface of the cell structure, the amount of cancer cells contained in the biological tissue or the enzyme-treated product of the biological tissue may be confirmed prior to sorting of the cancer cells. Cancer cells can be sorted by using the expression of a cancer cell-specific protein or an increase in enzyme activity as a cancer marker. The cancer marker is not particularly limited, and for example, when a protein specifically expressed in cancer cells such as EpCAM, CEA, Cytokeratin, and HER2 is used as a cancer marker, cancer cells can be visualized by immunohistochemical (IHC) staining or immunofluorescence (IF) staining using an antibody against them. Further, when the enzyme activity of γ-glutamyl transpeptidase or β-galactosidase which is elevated in cancer cells is used as a cancer marker, these enzyme activities can be measured using a fluorescent probe such as ProteoGREEN (registered trademark, manufactured by GORYO Chemical, Inc.) and GlycoGREEN (registered trademark, manufactured by GORYO Chemical, Inc.).

Sorting of cancer cells can be performed by techniques such as flow cytometry, magnetic separation, dielectrophoresis, size fractionation and density gradient fractionation, and the sorting method can be appropriately determined based on the organ from which the original patient tumor is derived, the clinical background, various previous test results, and the like. In the case of using flow cytometry, cancer cells can be sorted by separating cells that are positive in a staining treatment, after staining with IF or a fluorescent probe. Further, in flow cytometry, since live cells can also be distinguished from dead cells from the values of forward scattered light and side scattered light, it is possible to sort and recover live cancer cells more efficiently. Moreover, when using magnetic separation, cells are magnetically labeled with an antibody, but any of a positive selection method that magnetically recovers labeled cancer cells and a negative selection method that magnetically removes labeled stromal cells can be selected. In addition, when using dielectrophoresis and/or density gradient fractionation, it is preferable to understand in advance the dielectric characteristics and/or density gradient characteristics of the cell type used for the construction of stromal cells.

Further, before culturing on the top surface of the cell structure, the cells in the biological tissue may be labeled with a fluorescent material or the like in advance. All cells in the biological tissue may be labeled, or only specific cells for the purpose of primary culture may be labeled. The cell labeling method is not particularly limited, and can be appropriately selected from various labeling methods known in the art. For example, when cancer cells in a biological tissue are primary cultured, fluorescent labeling and the like using the CellTracker (registered trademark, manufactured by Thermo Fisher Scientific) or PKH Cell Linker Kit (Sigma-Aldrich) can be suitably used for labeling the cancer cells in the biological tissue. The labeling of the cancer cells may be performed on the biological tissue itself, or may be performed on a fragmented biological tissue or an enzyme-treated product of the fragmented biological tissue. Moreover, when sorting cancer cells from a biological tissue or its enzyme-treated product, the cancer cells after a selection process may be labeled.

EXAMPLES

Hereinafter, the above-described embodiment of the present invention will be specifically described by way of examples. However, the present invention is in no way limited by these examples, and a number of modifications can be made by those with ordinary knowledge in the field of art without departing from the gist of the present invention.

In the following examples, collagen I was used as collagen unless otherwise specified.

Example 1

A cell line established from a tumor cell collected from a cancer patient was cultured on the top surface of a cell structure containing stromal cells, and compared with cases where it was cultured in a normal culture medium and a primary culture medium.

<Cancer Cell Line>

A cell line JC-004 derived from a colorectal cancer patient (established from a surgical specimen at the Japanese Foundation for Cancer Research) was used as a cancer cell line. This patient-derived cancer cell line was constructed as follows.

First, a tumor tissue collected from a cancer patient was mechanically fragmented, and then the fragmented product was treated using collagenase/dispase (manufactured by Roche Diagnostics) and Dnase I (manufactured by Thermo Fisher Scientific). Subsequently, for the establishment, the obtained enzyme-treated product was cultured in StemPro medium (registered trademark, manufactured by Thermo Fisher Scientific), which was a serum-free medium for stem cells, supplemented with a ROCK inhibitor, Y-27632. The established cancer cell line was cultured using this medium until it was used in the present experiment.

<Construction of Cell Structure>

A cell structure including a vascular network structure was constructed using two types of cells, i.e., normal human dermal fibroblasts (NHDFs) (product number: CC-2509, manufactured by Lonza) and human umbilical vein endothelial cells (HUVECs) (product number: CC-2517A, manufactured by Lonza). A Transwell cell culture insert (product number: #3470, manufactured by Corning Incorporated) was used as a cell culture vessel, and a 10% by volume FBS (product number: #35-010-CV, manufactured by Corning Incorporated) and 1% by volume penicillin/streptomycin (product number: 168-23191, manufactured by Wako Pure Chemical Industries, Ltd.)-containing D-MEM (product number: 043-30085, manufactured by Wako Pure Chemical Industries, Ltd.) was used as a culture medium.

First, NHDFs and HUVECs were suspended in a tris-hydrochloric acid buffer containing heparin and collagen (0.05 mg/mL heparin, 0.05 mg/mL collagen, and 50 mM Tris, pH: 7.4) to prepare a cell suspension (step (a)). The cell suspension was centrifuged at room temperature at 1,200 rpm for 3 minutes, and after removing the supernatant, resuspended in an appropriate amount of culture medium (step (a'-1) and step (a'-2)). Subsequently, this cell suspension was seeded in a Transwell cell culture insert so that the number of cell layers was 20 (step (b)), and then the Transwell cell culture insert was centrifuged at room temperature at 400×g for 1 minute. Thereafter, an appropriate amount of culture medium was added to the Transwell cell culture insert, followed by culturing for 24 hours in a $CO_2$ incubator (37° C., 5% $CO_2$) (step (c)). As a result, a cell structure formed of 20 cell layers and having a vascular network structure was constructed.

It should be noted that in this example, the cell structure was produced so that the number of NHDFs was $2\times10^6$ cells/well and the number of HUVECs was 1.5% of the total number of NHDFs.

<Seeding of Cancer Cells>

First, the patient-derived cell line JC-004 was fluorescently labeled using a PKH67 cell linker kit. Thereafter, PKH26-labeled JC-004 was suspended in an appropriate amount of D-MEM medium (with 10% FBS) or Y-27632-containing StemPro medium, and seeded on the top surface of a cell structure constructed in a 24-well Transwell cell culture insert. Then, it was cultured for 2 weeks, while replacing the medium appropriately. As a control, PKH26-labeled JC-004 suspended in an appropriate amount of D-MEM medium (with 10% FBS) or Y-27632-containing StemPro medium was seeded and cultured in a 24-well Transwell cell culture insert in which no cell structure was constructed.

<Morphology Evaluation>

The cultured cancer cells were observed with a fluorescence microscope to confirm growth. The fluorescence image of each cancer cell is shown in FIG. 1.

In FIG. 1, one indicated as "no stroma" is a sample seeded and cultured directly on the culture insert.

Further, in FIG. 1, one indicated as "on 3D tissue" is a sample seeded and cultured on the top surface of the cell structure.

Moreover, one indicated as "DMEM" is a sample cultured in D-MEM medium (with 10% FBS), and one indicated as "ES medium" is a sample cultured in Y-27632-containing StemPro medium.

As a result, although the sample seeded and cultured directly on the culture insert grew without any problems in Y-27632-containing StemPro medium, almost no cells remained on the culture insert in D-MEM medium (with 10% FBS). On the other hand, in the sample seeded and cultured on the top surface of the cell structure containing stromal cells, although morphological differences were observed depending on the media, it was confirmed that the cancer cells were growing on both media.

Example 2

Cancer cells in a patient tumor tissue removed by surgery were cultured in a normal culture medium on the top surface of the cell structure containing stromal cells. As the culture medium, D-MEM medium containing 10% FBS was used.

<Cancer Cells in Patient Tumor Tissue>

The cancer cells in the patient tumor tissue were prepared as follows. First, a tumor tissue (JC-115) removed from a colorectal cancer patient at the Japanese Foundation for Cancer Research was mechanically fragmented, followed by an enzyme treatment with collagenase/dispase and Dnase I in the same manner as in Example 1, and was then thoroughly washed to prevent contamination. Subsequently, cancer cells (patient tumor tissue-derived JC-115 cells) in the obtained enzyme-treated product were fluorescently labeled using a PKH67 cell linker kit.

<Construction of Cell Structure>

A cell structure formed from NHDFs and HUVECs and having a vascular network structure, a cell structure formed only from NHDFs and not having a vascular network structure, and a cell structure formed from only one layer of HUVECs (two-dimensional culture) were each constructed on a culture substrate (in a cell culture vessel). The same cell culture vessel, NHDFs, HUVECs, and culture medium as those used in Example 1 were used.

A 20-layer cell structure formed from NHDF and HUVEC and having a vascular network structure was constructed in the same manner as the cell structure constructed in Example 1.

A 20-layer cell structure formed only from NHDF was constructed in the same manner as the cell structure constructed in Example 1 except that the cell suspension was prepared by suspending NHDF in a tris-hydrochloric acid buffer containing heparin and collagen (0.05 mg/mL heparin, 0.05 mg/mL collagen, and 50 mM Tris, pH: 7.4).

The cell structure formed from only one layer of HUVECs was constructed by seeding and culturing HUVECs suspended in a tris-hydrochloric acid buffer containing heparin and collagen (0.05 mg/mL heparin, 0.05 mg/mL collagen, and 50 mM Tris, pH: 7.4), directly in a 24-well Transwell cell culture insert so that the number of cell layers was one.

<Seeding of Cancer Cells>

Fluorescently labeled JC-115 cells derived from a patient tumor tissue were suspended in an appropriate amount of D-MEM medium (with 10% FBS) and seeded on the top surface of the cell structure constructed in a 24-well Transwell cell culture insert. Then, it was cultured for 2 weeks, while replacing the medium appropriately. As a control, fluorescently labeled JC-115 cells suspended in an appropriate amount of D-MEM medium (with 10% FBS) were seeded and cultured in a 24-well Transwell cell culture insert in which no cell structure was constructed.

<Morphology Evaluation>

Figure 2:
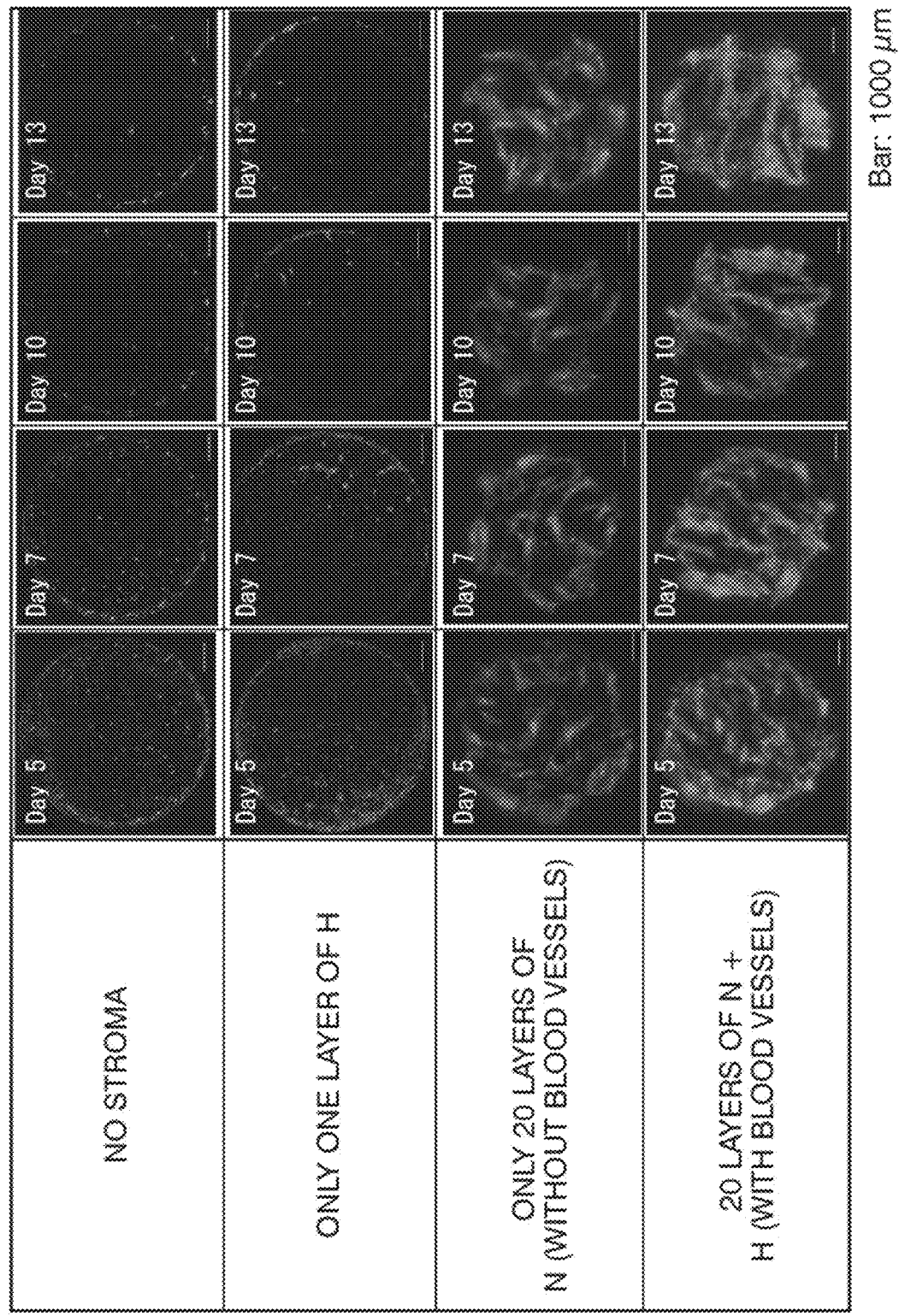
FIG. 2 shows fluorescence images of patient tumor tissue-derived JC-115 cells labeled with PKH on day 5, day 7, day 10, and day 13 from the start of the culture in Example 2.

The cultured cancer cells were observed with a fluorescence microscope on the fifth, seventh, tenth, and thirteenth days from the start of the culture to confirm growth. FIG. 2 shows fluorescence images of cancer cells in the same sample observed over time.

In FIG. 2, one indicated as "no stroma" is a sample seeded and cultured directly on the culture insert.

In FIG. 2, one indicated as "only one layer of H" is a sample cultured on the top surface of the cell structure formed from only one layer of HUVECs.

In FIG. 2, one indicated as "only 20 layers of N (without blood vessels)" is a sample cultured on the top surface of a 20-layer cell structure formed only from NHDFs.

In FIG. 2, one indicated as "20 layers of N+H (with blood vessels)" is a sample cultured on the top surface of a 20-layer cell structure formed from NHDFs and HUVECs.

As a result of observing the same sample over time, it was found that in the sample without stroma, the fluorescently labeled cells gradually decreased, although they could be confirmed for a certain period of time after seeding.

Further, in the sample seeded on the two-dimensional HUVEC culture (the sample of "only one layer of H" in FIG. 2), although the fluorescently labeled cells decreased to the same extent as in the sample of "no stroma" as the culture period increased, a larger number of fluorescently labeled cells were confirmed than those in the sample without stroma on day 5 of the culture. That is, it can be said that the two-dimensional HUVEC culture has an effect of assisting cell adhesion in the early stage of the culture, although it has a poor effect in enhancing the growth of primary cultured cancer cells.

In the samples seeded on the top surface of the 20-layer cell structure containing NHDFs, in both of the cell structure in which the vascular network structure was constructed (the sample of "20 layers of N+H (with blood vessels)" in FIG. 2) and the cell structure in which the vascular network structure was not constructed (the sample of "only 20 layers of N (without blood vessels)" in FIG. 2), a larger number of fluorescently labeled cells were confirmed than those in the sample without stroma on day 5 of the culture.

Furthermore, a marked increase or decrease in the number of fluorescently labeled cells was not observed between the cell structure in which the vascular network structure was constructed and the cell structure in which the vascular network structure was not constructed within 2 weeks from day 5 of the culture.

In other words, it was suggested that culturing on the top surface of a three-dimensional cell structure containing stromal cells had a positive effect on the growth of primary cultured cancer cells; and had both the effect of assisting cell adhesion in the early stage of the culture and the effect of enhancing the growth of primary cultured cancer cells.

Example 3

Cancer cells in a patient tumor tissue removed by surgery were cultured on the top surface of the cell structure containing stromal cells. As the culture medium, D-MEM medium containing 10% FBS or StemPro medium containing Y-27632 was used.
<Cancer Cells in Patient Tumor Tissue>
The cancer cells in the patient tumor tissue were prepared as follows. First, a tumor tissue (JC-121) removed from a colorectal cancer patient at the Japanese Foundation for Cancer Research was mechanically fragmented, followed by an enzyme treatment with collagenase/dispase and Dnase I in the same manner as in Example 1, and was then thoroughly washed to prevent contamination.
<Construction of Cell Structure>
A 20-layer cell structure formed from NHDFs and HUVECs and having a vascular network structure was constructed in the same manner as the cell structure constructed in Example 1.
<Seeding of Cancer Cells>
Patient tumor tissue-derived JC-121 cells were suspended in an appropriate amount of D-MEM medium (with 10% FBS) or Y-27632-containing StemPro medium and seeded on the top surface of the cell structure constructed in a 24-well Transwell cell culture insert. Thereafter, they were cultured in D-MEM medium (with 10% FBS) or StemPro medium containing Y-27632 for 2.5 weeks while appropriately replacing the medium.
<Morphology Evaluation>
After removing the medium from the cultured cell structure, it was washed with PBS and fixed with 10% neutral buffered formalin. Thereafter, cancer cells in the sample were visualized with a marker for colorectal cancer and evaluated. More specifically, immunofluorescence staining was performed using an anti-non-phosphorylated (activated) β-catenin antibody and an anti-CD31 antibody, and nuclear staining with DAPI was further performed. Non-phosphorylated β-catenin is a protein that specifically accumulates in cancer cells, and CD31 is a protein that is specifically expressed in vascular endothelial cells. The cell structure after staining was observed with a fluorescence microscope.

Figure 3:
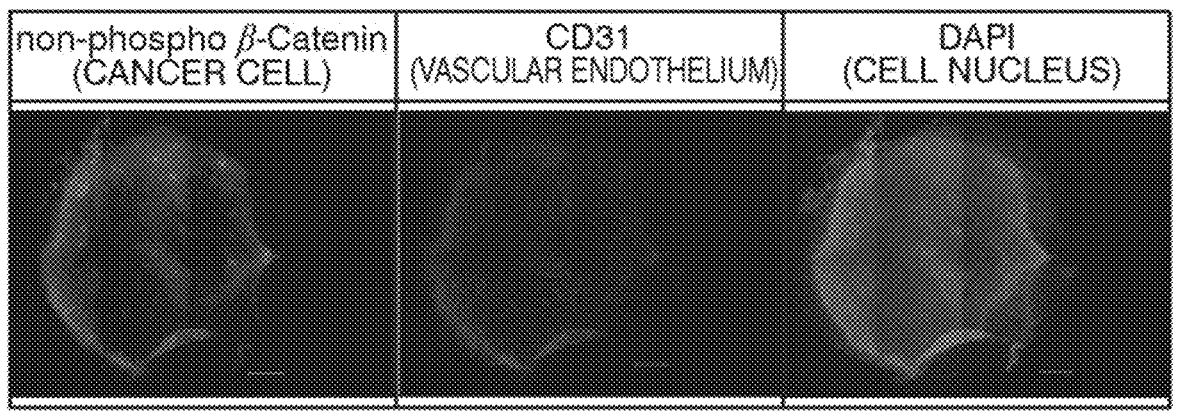
FIG. 3 shows fluorescence images of patient tumor tissue-derived JC-121 cells after culturing for 2.5 weeks in D-MEM medium (with 10% FBS) in Example 3.

FIG. 3 shows a stained image of the cell structure cultured in D-MEM medium (with 10% FBS).

Figure 4:
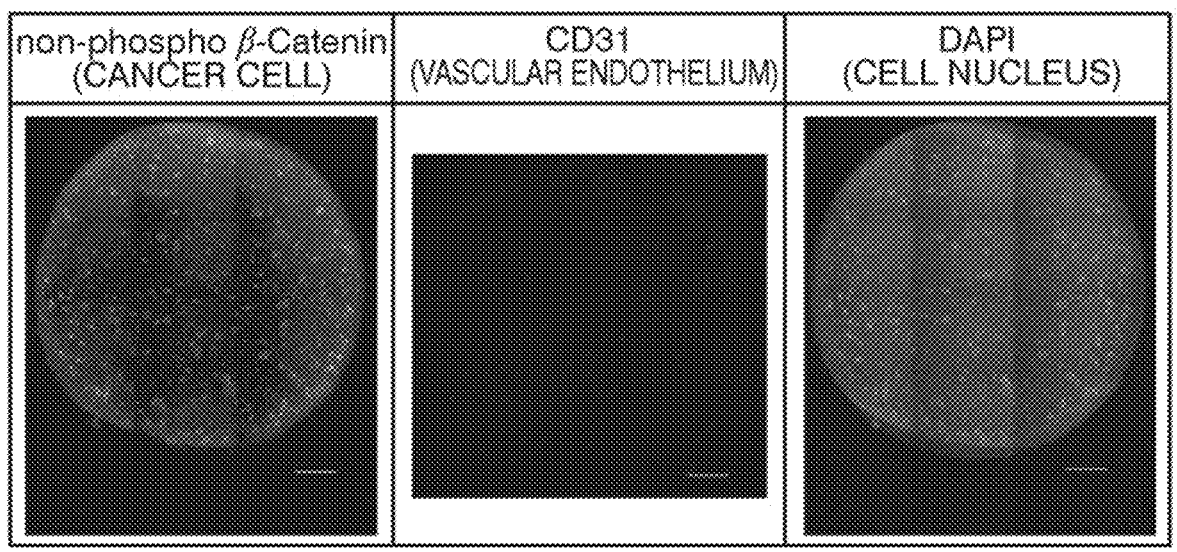
FIG. 4 shows fluorescence images of the patient tumor tissue-derived JC-121 cells after culturing for 2.5 weeks in Y-27632-containing StemPro medium in Example 3.

Further, FIG. 4 shows a stained image of the cell structure cultured in Y-27632-containing StemPro medium.

As shown in FIG. 3 and FIG. 4, it was confirmed that cancer cells were definitely present since the accumulation of non-phosphorylated β-catenin, which was not seen in normal cells, was observed in the cell structures cultured in both culture media. That is, it was confirmed that not only fibroblasts but also cancer cells grew among the cells derived from the patient tumor tissue.

Example 4

Cancer cells in a patient tumor tissue removed by surgery together with other cells or only the cancer cells after sorting and recovery were each cultured on the top surfaces of a plurality of cell structures having different numbers of cell layers. As the culture medium, D-MEM medium containing 10% FBS was used.
<Cancer Cells in Patient Tumor Tissue>
The cancer cells in the patient tumor tissue were prepared as follows. First, a tumor tissue (JC-052-3-liv) removed from a patient with liver cancer (metastatic lesion from colorectal cancer) at the Japanese Foundation for Cancer Research was mechanically fragmented, followed by an enzyme treatment with collagenase/dispase and Dnase I in the same manner as in Example 1, and was then thoroughly washed to prevent contamination.
<Construction of Cell Structure>
A 20-layer cell structure formed from NHDFs and HUVECs and having a vascular network structure was constructed in the same manner as the cell structure constructed in Example 1. In addition, cell structures formed from NHDFs and HUVECs and having a vascular network structure were constructed in the same manner except that the number of cell layers was 1, 5, or 10.

Further, a 20-layer cell structure formed from NHDFs and not having a vascular network structure was constructed in the same manner as the cell structure constructed in Example 2. Moreover, cell structures formed from NHDFs and not having a vascular network structure were constructed in the same manner except that the number of cell layers was 1, 5, or 10.
<Seeding of Cancer Cells>
Patient tumor tissue-derived JC-052-3-liv cells were suspended in an appropriate amount of D-MEM medium (with 10% FBS) and seeded on the top surface of the cell structure constructed in a 24-well Transwell cell culture insert. Thereafter, they were cultured in D-MEM medium (with 10% FBS) for 5 days while appropriately replacing the medium.

As a control, JC-052-3-liv cells suspended in an appropriate amount of D-MEM medium (with 10% FBS) or StemPro medium containing Y-27632 were seeded and cultured in a 24-well Transwell cell culture insert in which no cell structure was constructed.
<Enzyme Treatment and Measurement of EpCAM Positive Cells>
After removing the medium from the cultured cell structure, the cell structure was washed with PBS and treated with an enzyme included in the Tumor Dissociation Kit (manufactured by Miltenyi Biotec) to disperse the cells constituting the cell structure. Thereafter, the enzyme-treated product was subjected to immunofluorescence staining with an anti-EpCAM antibody, and the ratio of EpCAM positive cells was measured using an automated cell counter with a fluorescence filter.

For each cell structure, the relative number of cells after culture was calculated as the growth rate of JC-052-3-liv cells when the number of JC-052-3-liv cells (seeded on the top surface of the cell structure) before the start of culture was taken as 1.

Figure 5:
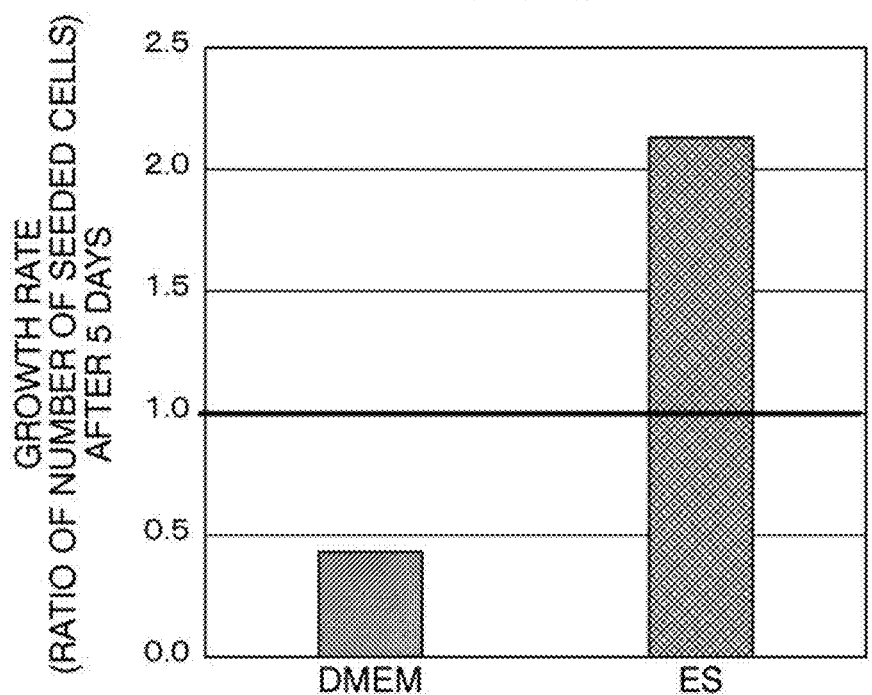
FIG. 5 is a diagram showing results of measuring the growth rate (ratio of number of seeded cells) of a sample after 5 days which is obtained by seeding JC-052-3-liv cells derived from a patient tumor tissue in a 24-well Transwell cell culture insert in which no cell structure is constructed and culturing for 5 days in Example 4.

FIG. 5 shows a calculation result of a sample seeded in a 24-well Transwell cell culture insert in which no cell structure is constructed.

Figure 6:
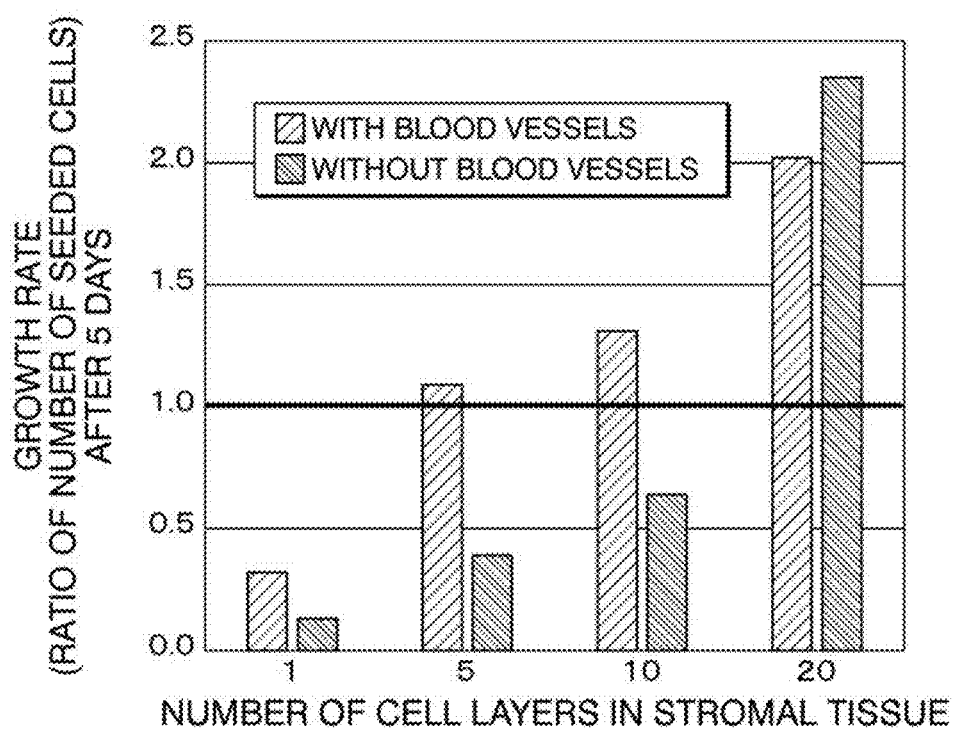
FIG. 6 is a diagram showing a measurement result of the growth rate (ratio of number of seeded cells) of a sample after 5 days which is obtained by seeding the JC-052-3-liv cells derived from a patient tumor tissue on the top surface of a cell structure containing stromal cells and culturing for 5 days in Example 4.

FIG. 6 shows a calculation result of a sample seeded on the top surface of the cell structure.

In FIG. 5, one indicated as "DMEM" is a sample cultured in D-MEM medium (with 10% FBS).

In FIG. 5, one indicated as "ES medium" is a sample cultured in Y-27632-containing StemPro medium.

Further, in FIG. 6, one indicated as "with blood vessel" shows the result of a cell structure having a vascular network structure.

In FIG. 6, one indicated as "without blood vessels" shows the result of a cell structure having no vascular network structure.

Figure 7:
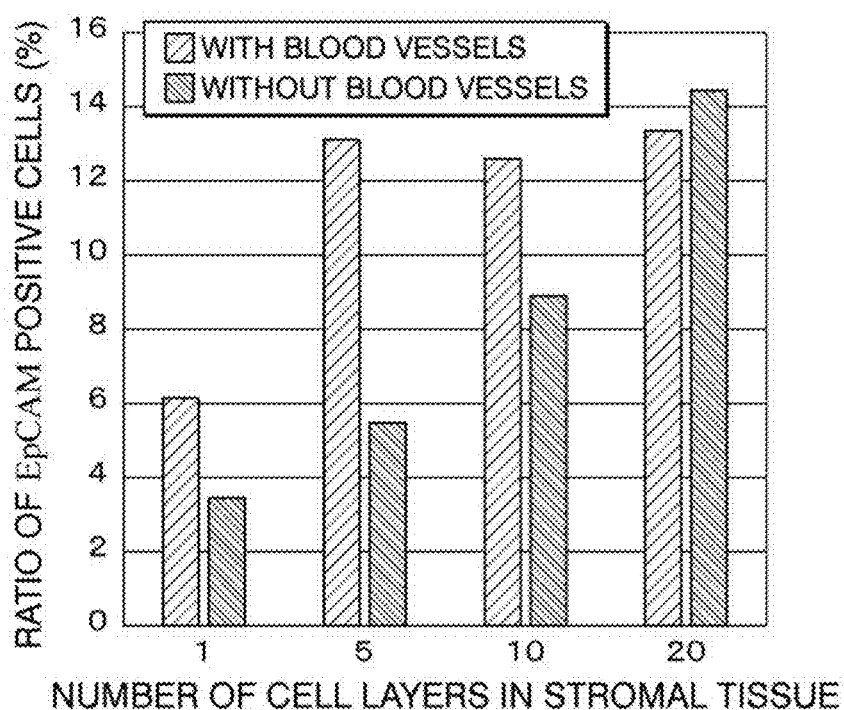
FIG. 7 is a diagram showing results of measuring a ratio of EpCAM positive cells with respect to a total number of cells (cell number ratio, %) in a sample obtained by seeding the JC-052-3-liv cells derived from a patient tumor tissue on the top surface of a cell structure containing stromal cells and culturing for 5 days in Example 4.

Further, FIG. 7 shows the ratio (%) of EpCAM positive cells (cells stained with an anti-EpCAM antibody) to the total number of cells in the sample seeded on the top surface of the cell structure.

As shown in FIG. 5, when seeded directly in a cell culture vessel, JC-052-3-liv cells were able to grow in Y-27632-containing StemPro medium, but were unable to grow in D-MEM medium (with 10% FBS). On the other hand, as shown in FIG. 6, when cultured on the top surface of the cell structure in D-MEM medium (with 10% FBS), in the cell structures having a vascular network structure, the growth rate after 5 days was 1 or more and proliferation of the seeded cells was observed when cultured in the cell structures having 5 or more layers. In the cell structures having no vascular network structure, the growth rate after 5 days was 1 or more and proliferation of the seeded cells was observed when cultured in the 20-layer cell structure.

As shown in FIG. 7, in the sample cultured on the top surface of the cell structure, EpCAM positive cells were observed regardless of the number of cell layers. From this result, it was confirmed that primary cultured cancer cells grew in D-MEM medium (with 10% FBS) by culturing on the top surface of the cell structure containing stromal cells.

<Measurement of EpCAM Positive Cells after Magnetic Separation>

Figure 8:
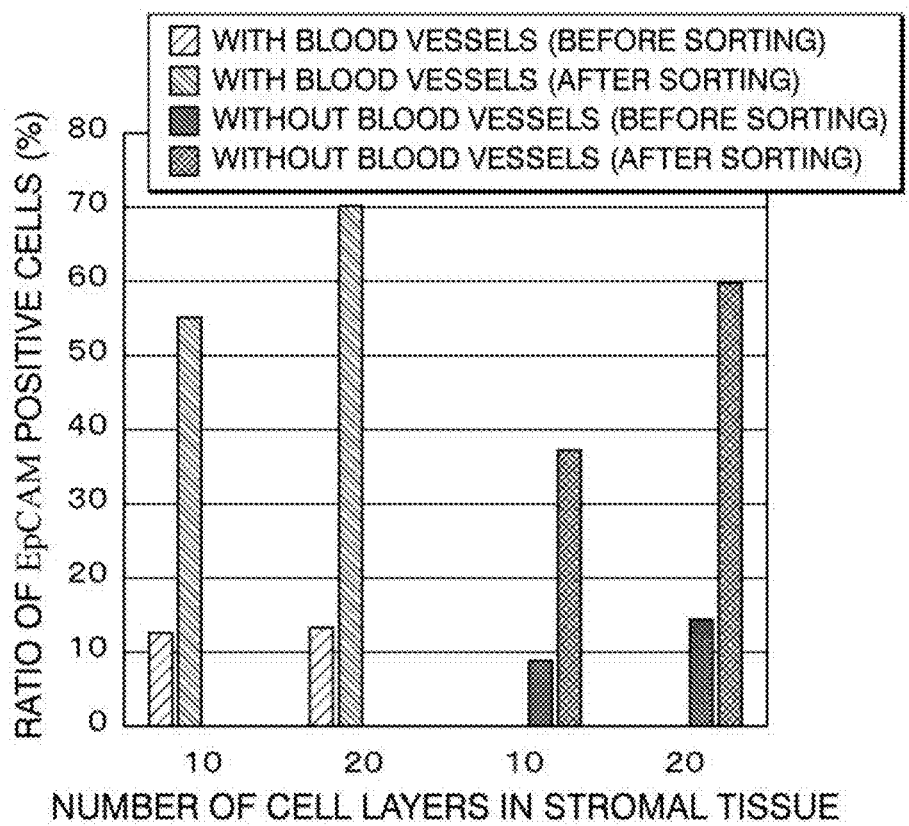
FIG. 8 is a diagram showing results of measuring a ratio (%) of the number of EpCAM positive cells with respect to the total number of cells before and after sorting and recovery for a sample obtained by culturing the JC-052-3-liv cells derived from a patient tumor tissue in a cell structure having 10 or 20 cell layers in Example 4.

Furthermore, NHDFs and HUVECs in the enzyme-treated product were magnetically labeled using the Tumor Cell Isolation Kit (manufactured by Miltenyi Biotec), and then the magnetically labeled cells were removed by negative selection, and cells other than NHDFs and HUVECs were sorted and recovered. Thereafter, the ratio of EpCAM positive cells in the sorted and recovered cells was measured using the aforementioned automated cell counter. FIG. 8 shows the measurement results of the ratio (%) of the number of EpCAM positive cells to the total number of cells after sorting and recovery for samples cultured in cell structures having 10 and 20 cell layers.

For comparison, the results before sorting and recovery are also shown at the same time. As a result, the ratio of EpCAM positive cells increased before and after sorting and recovery. From this result, it was shown that it was possible to concentrate and recover primary cultured cancer cells.

<Staining of Patient Tumor Tissue-Derived JC-052-3-Liv Cells with Anti-EpCAM Antibody>

Immunofluorescence staining with an anti-EpCAM antibody was performed in the same manner as described above for JC-052-3-liv cells seeded in a 24-well Transwell cell culture insert in which no cell structure was constructed and cultured in D-MEM medium (with 10% FBS) for 5 days.

Figure 9:
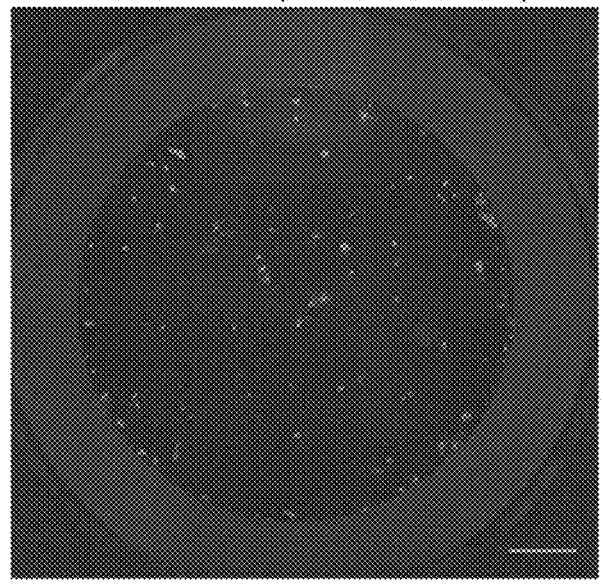
FIG. 9 is a fluorescence image obtained by immunofluorescence staining JC-052-3-liv cells directly seeded in a cell culture vessel with an anti-EpCAM antibody in Example 4.

The staining result is shown in FIG. 9. As a result, since the presence of EpCAM positive cells was confirmed, it is clear that JC-052-3-liv cells, which are cancer cells derived from the patient tumor tissue, are EpCAM positive cells.

<Staining of NHDFs and HUVECs with Anti-EpCAM Antibody>

Figure 10:
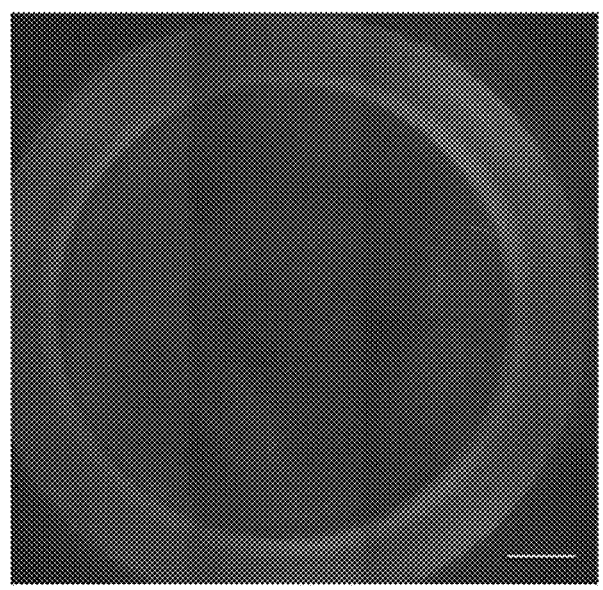
FIG. 10 is a fluorescence image obtained by immunofluorescence staining a 20-layer cell structure formed from NHDFs and HUVECs with an anti-EpCAM antibody in Example 4.

Immunofluorescence staining with an anti-EpCAM antibody was performed in the same manner as described above for a 20-layer cell structure formed from NHDFs and HUVECs and having a vascular network structure. The staining result is shown in FIG. 10. As a result, it was confirmed that NHDFs and HUVECs were not stained with the anti-EpCAM antibody.

Example 5

It was examined whether growth of primary cultured cancer cells was possible even when using various "general media" other than DMEM by using patient tumor tissue-derived cells (PDC) derived from a metastatic lesion from colorectal cancer (liver cancer).

Patient tumor tissue-derived cells derived from a metastatic lesion from colorectal cancer (liver cancer) together with other cells or only the cancer cells after sorting and recovery were cultured on the top surface of a cell structure with 20 cell layers.

<Cancer Cells in Patient Tumor Tissue>

The patient tumor tissue-derived cells (PDC) were prepared as follows.

First, a tumor tissue (JC039-2-Liv) removed from a patient with liver cancer (metastatic lesion from colorectal cancer) at the Japanese Foundation for Cancer Research was mechanically fragmented, followed by an enzyme treatment with collagenase/dispase and Dnase I in the same manner as in Example 1, and was then thoroughly washed to prevent contamination.

Similarly, a tumor tissue (JC047-2-Liv) removed from a patient with liver cancer (metastatic lesion from colorectal cancer) at the Japanese Foundation for Cancer Research was mechanically fragmented, followed by an enzyme treatment with collagenase/dispase and Dnase I in the same manner as in Example 1, and was then thoroughly washed to prevent contamination.

<Construction of Cell Structure>

Similar to the cell structure constructed in Example 1, a 20-layer cell structure formed from NHDFs and HUVECs (NHDFs: $2 \times 10^6$ cells/well; HUVECs: 1.5% of the total number of NHDFs) and having a vascular network structure was constructed.

<Seeding of Cancer Cells>

Patient tumor tissue-derived JC039-2-Liv cells were suspended in an appropriate amount of D-MEM medium (with 10% FBS) and seeded on the top surface of the cell structure constructed in a 24-well Transwell cell culture insert. Thereafter, they were cultured in D-MEM medium (with 10% FBS) for 14 days while appropriately replacing the medium.

The patient tumor tissue-derived JC039-2-Liv cells were cultured for 14 days using each of the following three media in place of D-MEM medium.

It should be noted that the patient tumor tissue-derived JC039-2-Liv cells were cultured in the same manner as in the case of using the above D-MEM medium except that any one of the following three media was used instead of the D-MEM medium.

RPMI-1640 medium (a medium used as a high nutrient medium that can be widely used for mammalian cells)

McCoy's 5A medium (a medium developed for culturing lymphocytes and also often used for cancer cell lines)

ES medium (in this example, Y-27632-containing Stem-Pro medium was used. It is a medium often used for primary culture of cancer clinical specimens and used for establishment and maintenance of patient-derived cell lines.)

It should be noted that the number of cells derived from the patient tumor tissue and seeded on the cell structure was $1\times10^4$ cells/well.

As in the case of the above-mentioned patient tumor tissue-derived JC039-2-Liv cells, the patient tumor tissue-derived JC047-2-Liv cells were seeded on the top surface of the cell structure and cultured for 14 days using each of four types of media; i.e., D-MEM medium (with 10% FBS), RPMI-1640 medium, McCoy's 5A medium, and ES medium.

It should be noted that the number of cells derived from the patient tumor tissue and seeded on the cell structure was $1\times10^4$ cells/well.

As a control, each of the patient tumor tissue-derived cells (JC039-2-Liv cells or JC047-2-Liv cells) were seeded and cultured in a collagen-coated 6-well plate in which no cell structure was constructed, using an appropriate amount of the above four media (D-MEM medium, RPMI-1640 medium, McCoy's 5A medium, or ES medium).

It should be noted that the number of cells derived from the patient tumor tissue and seeded in the collagen-coated 6-well plate was $1\times10^5$ cells/well.

<Enzyme Treatment and Measurement of EpCAM Positive Cells>

After removing the medium from the cultured cell structure or the collagen-coated 6-well plate in which no cell structure was constructed by the same method as in Example 4, it was washed with PBS and treated with an enzyme included in the Tumor Dissociation Kit (manufactured by Miltenyi Biotec) to disperse the cells constituting the cell structure. Thereafter, the enzyme-treated product was subjected to immunofluorescence staining with an anti-EpCAM antibody, and the ratio of EpCAM positive cells was measured using an automated cell counter with a fluorescence filter.

Figure 11:
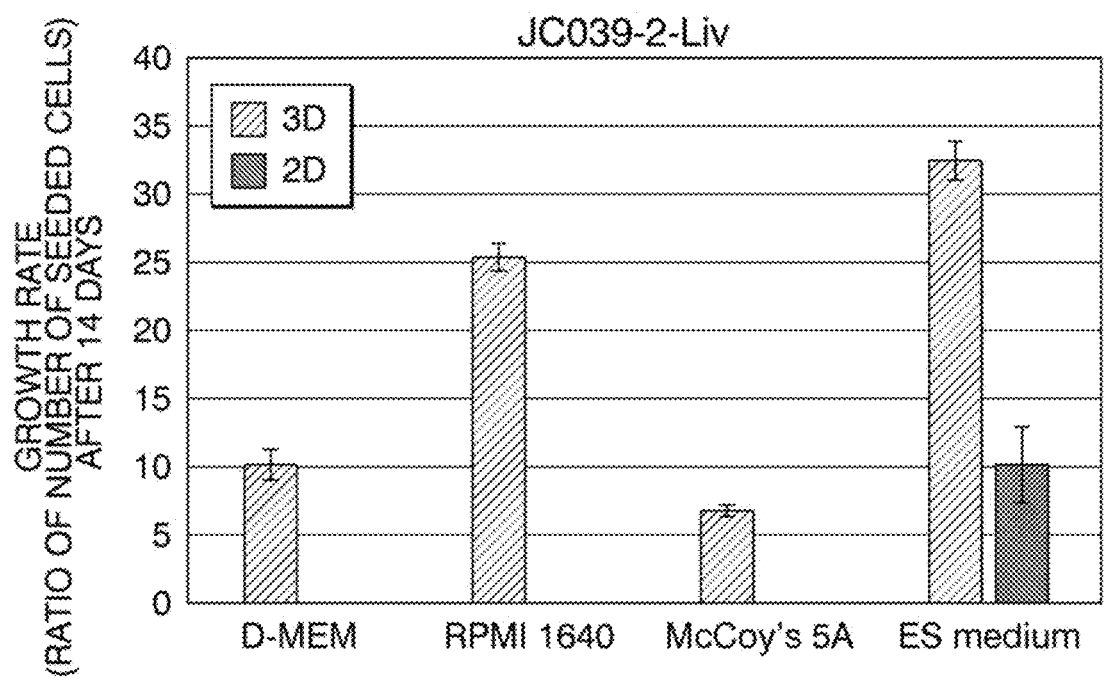
FIG. 11 is a diagram showing a comparison of results of measuring the growth rates (ratio of number of seeded cells) after 14 days in a sample (1) obtained by seeding JC039-2-Liv cells derived from a patient tumor tissue on the top surface of a cell structure containing stromal cells and culturing for 14 days using each of four types of media; and a sample (2) obtained by seeding JC039-2-Liv cells derived from a patient tumor tissue in a collagen-coated 6-well plate in which no cell structure is constructed and culturing for 14 days using each of four types of media, in Example 5.

For each cell structure, the relative number of cells after culture was calculated as the growth rate of cells (JC039-2-Liv cells or JC047-2-Liv cells) when the number of cells (the number of JC039-2-Liv cells or the number of JC047-2-Liv cells) (seeded on the top surface of the cell structure) before the start of culture was taken as 1. FIG. 11 shows the result of calculating the growth rate of a sample (which is an example indicated as 3D in FIG. 11 using a cell structure having a three-dimensional structure) obtained by seeding JC039-2-Liv cells derived from a patient tumor tissue on the top surface of a cell structure containing stromal cells and culturing for 14 days using each of the above four types of media.

Further, as a control, FIG. 11 shows the result of calculating the growth rate of a sample (indicated as 2D in FIG. 11 which corresponds to the case with no stroma) obtained by seeding JC039-2-Liv cells derived from a patient tumor tissue in a collagen-coated 6-well plate in which no cell structure was constructed and culturing for 14 days using each of the above four types of media.

In other words, FIG. 11 is a diagram showing a comparison of results of measuring the growth rates (ratio of number of seeded cells) after 14 days in a sample (1) obtained by seeding JC039-2-Liv cells derived from a patient tumor tissue on the top surface of a cell structure containing stromal cells and culturing for 14 days using each of four types of media; and a sample (2) obtained by seeding JC039-2-Liv cells derived from a patient tumor tissue in a collagen-coated 6-well plate in which no cell structure is constructed and culturing for 14 days using each of four types of media, in Example 5.

Figure 12:
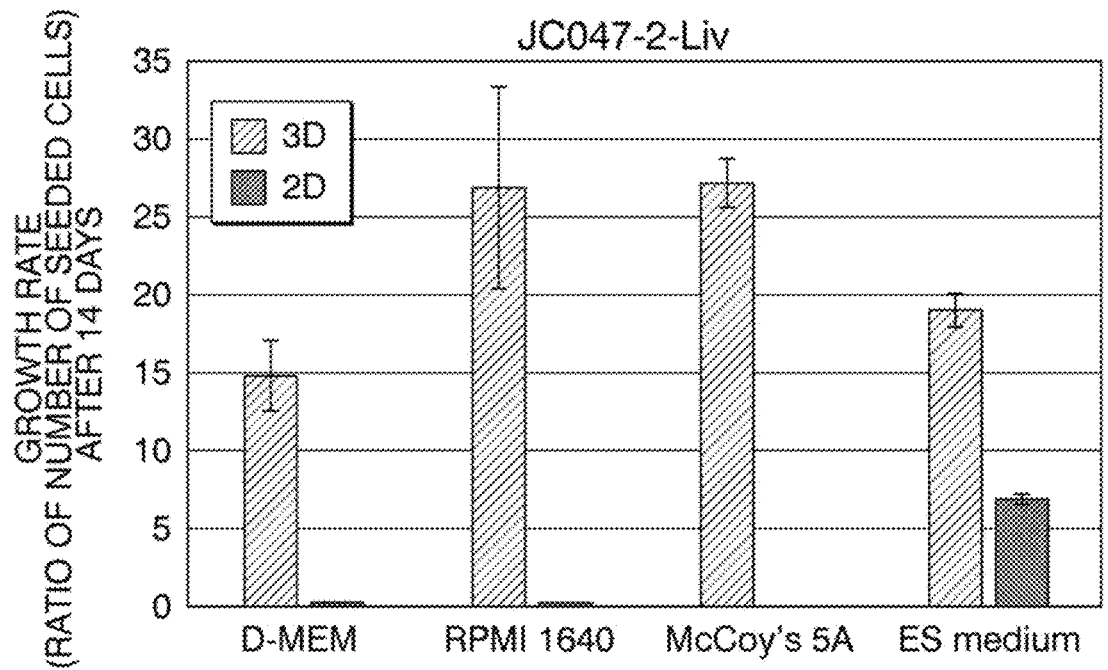
FIG. 12 is a diagram showing a comparison of results of measuring the growth rates (ratio of number of seeded cells) after 14 days in a sample (1) obtained by seeding JC047-2-Liv cells derived from a patient tumor tissue on the top surface of a cell structure containing stromal cells and culturing for 14 days using each of four types of media; and a sample (2) obtained by seeding JC047-2-Liv cells derived from a patient tumor tissue in a collagen-coated 6-well plate in which no cell structure is constructed and culturing for 14 days using each of four types of media, in Example 5.

FIG. 12 shows the result of calculating the growth rate of a sample (which is an example indicated as 3D in FIG. 12 using a cell structure having a three-dimensional structure) obtained by seeding JC047-2-Liv cells derived from a patient tumor tissue on the top surface of a cell structure containing stromal cells and culturing for 14 days using each of the above four types of media.

Further, as a control, FIG. 12 shows the result of calculating the growth rate of a sample (indicated as 2D in FIG. 12 which corresponds to the case with no stroma) obtained by seeding JC047-2-Liv cells derived from a patient tumor tissue in a collagen-coated 6-well plate in which no cell structure was constructed and culturing for 14 days using each of the above four types of media.

That is, FIG. 12 is a diagram showing a comparison of results of measuring the growth rates (ratio of number of seeded cells) after 14 days in a sample (1) obtained by seeding JC047-2-Liv cells derived from a patient tumor tissue on the top surface of a cell structure containing stromal cells and culturing for 14 days using each of four types of media; and a sample (2) obtained by seeding JC047-2-Liv cells derived from a patient tumor tissue in a collagen-coated 6-well plate in which no cell structure is constructed and culturing for 14 days using each of four types of media, in Example 5.

As shown in FIG. 11 and FIG. 12, in those cases where any of the two types of patient tumor tissue-derived cells (JC039-2-Liv cells, JC047-2-Liv cells) was used, when using the cell structure having a three-dimensional structure (3D in FIGS. 11 and 12), the growth rates exceeded 1.0 in any of the four types of media.

That is, when cancer cells were cultured using a cell structure having a three-dimensional structure, proliferation of the cancer cells was confirmed even when a general medium other than the D-MEM medium was used.

On the other hand, in the case of 2D in which no cell structure was constructed (in the case of "no stroma"), when a medium other than the ES medium was used, the number of recovered cells was smaller than the number of seeded cells, and it was confirmed that patient tumor tissue-derived cancer cells tended not to grow in general media.

According to this example, it was confirmed that when the cell structure according to the above embodiment was used, cancer cells derived from a patient tumor tissue were able to grow even when a "general medium" other than the D-MEM medium was used.

In other words, according to this example, when the cell structure according to the above embodiment was used, the possibility that primary cultured cancer cells could be cultured regardless of the medium was shown.

Example 6

Next, using primary cultured tumor cells, the relationship between the thickness of the 3D tissue and the presence or absence of vascular network in the cell structure and the growth rate, and the effect of the cancer type were examined.

<Cancer Cells in Patient Tumor Tissue>

The cancer cells in the patient tumor tissue were prepared as follows.

Sample Preparation of Cancer Cells Derived from Primary Lesion of Colorectal Cancer First, a tumor tissue (primary lesion of colorectal cancer, JC406-1-TT) removed from a colorectal cancer patient at the Japanese Foundation for Cancer Research was mechanically fragmented, followed by an enzyme treatment with collagenase/dispase and Dnase I in the same manner as in Example 1. Then, a flow-through fraction obtained after fractionation with a filter having a pore size of 100 μm was obtained and thoroughly washed to prevent contamination.

Sample Preparation of Lung Cancer-Derived Cancer Cells

In addition, a tumor tissue (lung metastatic lesion from colorectal cancer, JC247-2-PUL) removed from a patient with lung cancer (metastatic lesion from colorectal cancer) at the Japanese Foundation for Cancer Research was mechanically fragmented, followed by an enzyme treatment with collagenase/dispase and Dnase I in the same manner as in Example 1. Then, a flow-through fraction obtained after fractionation with a filter having a pore size of 100 μm was obtained and thoroughly washed to prevent contamination.

<Construction of Cell Structure>

Cell Structure with Vascular Network Structure

A 20-layer cell structure formed from NHDFs and HUVECs and having a vascular network structure was constructed in the same manner as the cell structure constructed in Example 1. In addition, cell structures formed from NHDFs and HUVECs and having a vascular network structure were constructed in the same manner except that the number of cell layers was 1, 5, or 10.

Cell Structure without Vascular Network Structure

Further, a 20-layer cell structure formed from NHDFs and not having a vascular network structure was constructed in the same manner as the cell structure constructed in Example 2. Moreover, cell structures formed from NHDFs and not having a vascular network structure were constructed in the same manner except that the number of cell layers was 1, 5, or 10.

<Seeding of Cancer Cells>

Seeding of JC406-1-TT Cells Derived from Tumor Tissue of Colorectal Cancer Patient JC406-1-TT cells derived from a tumor tissue of colorectal cancer patient and obtained by the above fractionation were suspended in an appropriate amount of D-MEM medium (with 10% FBS) and seeded on the top surface of a 20-layer cell structure (cell structure formed from NHDFs and HUVECs and having a vascular network structure) constructed in a 24-well Transwell cell culture insert. Thereafter, they were cultured in D-MEM medium (with 10% FBS) for 14 days while appropriately replacing the medium.

Further, JC406-1-TT cells derived from a tumor tissue of colorectal cancer patient were cultured for 14 days each using RPMI-1640 medium instead of D-MEM medium by the same method.

Furthermore, JC406-1-TT cells derived from a tumor tissue of colorectal cancer patient were cultured for 14 days each using McCoy's 5A medium instead of D-MEM medium by the same method.

Similarly, JC406-1-TT cells were cultured using each of three types of media in each of the cell structures having 1 layer, 5 layers, and 10 layers.

Seeding of JC247-2-PUL Cells Derived from Tumor Tissue of Lung Cancer Patient

Further, JC247-2-PUL cells derived from a tumor tissue of lung cancer patient and obtained by the above fractionation were suspended in an appropriate amount of D-MEM medium (with 10% FBS) and seeded on the top surface of a 20-layer cell structure (cell structure formed from NHDFs and HUVECs and having a vascular network structure) constructed in a 24-well Transwell cell culture insert. Thereafter, they were cultured in D-MEM medium (with 10% FBS) for 14 days while appropriately replacing the medium.

Similarly, in each of the cell structures having 1 layer, 5 layers, and 10 layers (cell structures formed from NHDFs and HUVECs and having a vascular network structure), the JC247-2-PUL cells derived from a tumor tissue of lung cancer patient were cultured for 14 days in D-MEM medium (with 10% FBS) while appropriately replacing the medium.

Further, the JC247-2-PUL cells derived from a tumor tissue of lung cancer patient were also cultured for 14 days in D-MEM medium (with 10% FBS) while appropriately replacing the medium in a similar manner in cell structures (having 1 layer, 5 layers, 10 layers, or 20 layers) formed from NHDFs and not having a vascular network structure.

<Enzyme Treatment and Measurement of EpCAM Positive Cells>

In the same manner as in Example 4 and Example 5, after removing the medium from the cultured cell structure, the cell structure was washed with PBS and treated with an enzyme included in the Tumor Dissociation Kit (manufactured by Miltenyi Biotec) to disperse the cells constituting the cell structure. Thereafter, the enzyme-treated product was subjected to immunofluorescence staining with an anti-EpCAM antibody, and the ratio of EpCAM positive cells was measured using an automated cell counter with a fluorescence filter.

Figure 13:
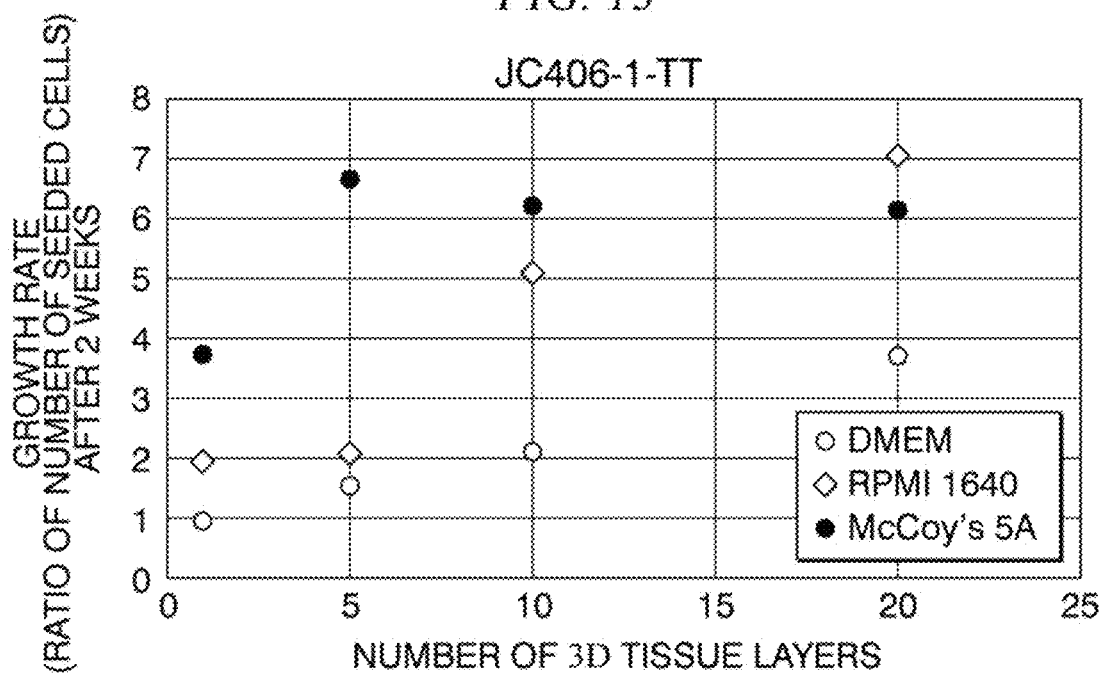
FIG. 13 is a diagram showing results of measuring the growth rate (ratio of number of seeded cells) after 14 days in a sample obtained by seeding JC406-1-TT cells derived from a patient tumor tissue (primary lesion of colorectal cancer) on the top surface of a cell structure containing stromal cells and culturing for 14 days using each of 3 types of media, when the number of 3D tissue layers of the constituting cell structure is changed in Example 6.

For each cell structure, the relative number of cells after culture was calculated as the growth rate of cells (JC406-1-TT cells or JC247-2-PUL cells) when the number of cells (the number of JC406-1-TT cells or the number of JC247-2-PUL cells) (seeded on the top surface of the cell structure) before the start of culture was taken as 1. FIG. 13 shows a change in the growth rate (%) after 2 weeks of JC406-1-TT cells with respect to a change in the number of layers of cell structures (the number of 3D tissue layers) formed from NHDFs and HUVECs and having a vascular network structure when each of three types of media (D-MEM medium, RPMI-1640 medium, and McCoy's 5A medium) is used.

In other words, FIG. 13 is a diagram showing results of measuring the growth rate (ratio of number of seeded cells) after 14 days in a sample obtained by seeding JC406-1-TT cells derived from a patient tumor tissue (primary lesion of colorectal cancer) on the top surface of a cell structure containing stromal cells and culturing for 14 days using each of 3 types of media, when the number of 3D tissue layers of the constituting cell structure is changed in Example 6.

Figure 14:
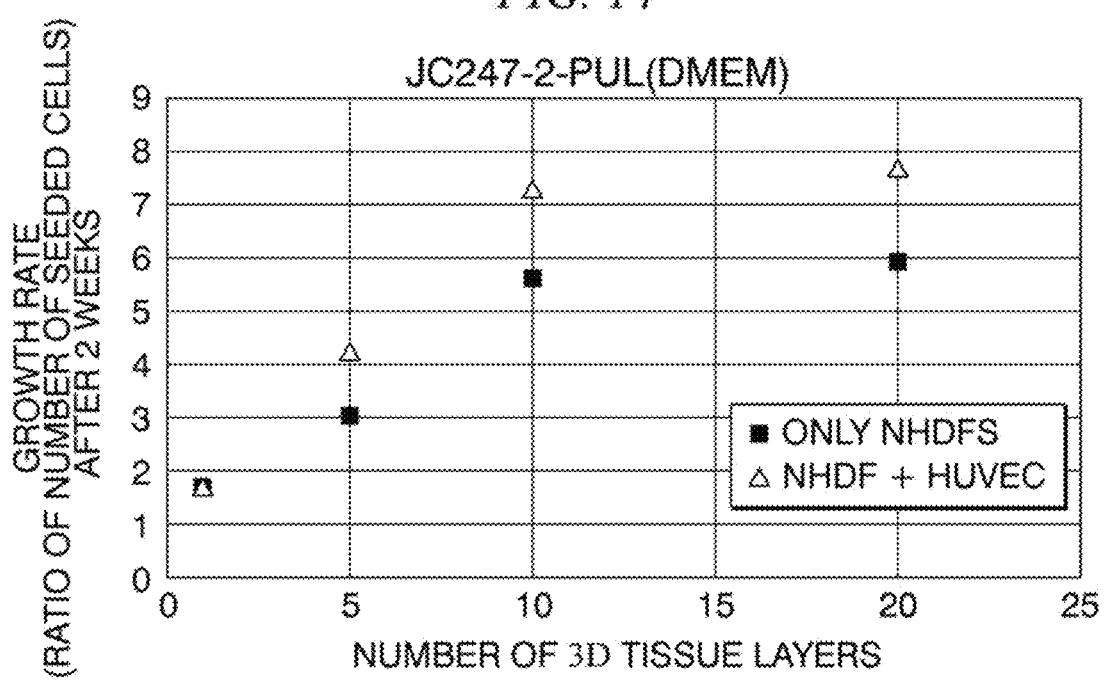
FIG. 14 is a diagram showing results of measuring the growth rate (ratio of number of seeded cells) after 14 days in a sample obtained by seeding JC247-2-PUL cells derived from a patient tumor tissue (lung metastatic lesion of colorectal cancer) on the top surface of a cell structure containing stromal cells and culturing for 14 days, when the number of 3D tissue layers of two types of cell structures (cell structures formed from NHDFs and not having a vascular network structure or cell structures formed from NHDFs and HUVECs and having a vascular network structure) is changed in Example 6.

Further, FIG. 14 is a diagram showing results of measuring the growth rate (ratio of number of seeded cells) after 14 days in a sample obtained by seeding JC247-2-PUL cells derived from a patient tumor tissue (lung metastatic lesion of colorectal cancer) on the top surface of a cell structure containing stromal cells and culturing for 14 days, when the number of 3D tissue layers of two types of cell structures (cell structures formed from NHDFs and not having a vascular network structure or cell structures formed from NHDFs and HUVECs and having a vascular network structure) is changed in Example 6.

When the relationship between the thickness of the 3D tissue and the presence or absence of vascular network in the cell structure and the growth rate was confirmed using the primary cultured tumor cells as described above, as shown in FIG. 13, the growth rate of cancer cells tended to improve as the number of 3D tissue layers increased in any of the media.

In addition, as shown in FIG. 14, according to this example, it was confirmed that when the cell structure according to the above embodiment was used, it was also possible to culture cancer cells in a similar manner in lung cancer (metastatic lesion from colorectal cancer, lung metastasis cases), in addition to colorectal cancer (primary lesion of colorectal cancer) and liver cancer (metastatic lesion from colorectal cancer, liver metastasis cases) as shown in Examples 1 to 5. Further, the growth rate of cancer cells also tended to improve in the lung cancer cells in the same manner as in the colorectal cancer cells as the number of 3D tissue layers in the cell structure increased.

Furthermore, as shown in FIG. 14, by comparing a cell structure formed from NHDFs and not having a vascular network structure with a cell structure formed from NHDFs and HUVECs and having a vascular network structure, it became clear that the cell growth rate tends to be higher on the tissue containing vascular endothelial cells than on the cell structure constituted only of fibroblasts.

It should be noted that as shown in FIG. 14, the tendency of the cell growth rate to increase as the number of 3D tissue layers in the cell structure increased was similar in both the cell structure formed from NHDFs and not having a vascular network structure and the cell structure formed from NHDFs and HUVECs and having a vascular network structure. That is, the tendency of the cell growth rate to improve as the number of 3D tissue layers in the cell structure increased was the same regardless of the presence or absence of the vascular network.

Example 7

In this example, the relationship between the ratio of vascular endothelial cells in 3D tissue and the proliferation rate of cancer cells was confirmed using primary cultured tumor cells.

<Cancer Cells in Patient Tumor Tissue>

The cancer cells in the patient tumor tissue were prepared as follows.

First, a tumor tissue (JC406-1-TT) removed from a patient with colorectal cancer (primary lesion of colorectal cancer) at the Japanese Foundation for Cancer Research was mechanically fragmented, followed by an enzyme treatment with collagenase/dispase and Dnase I in the same manner as in Example 1, and was then thoroughly washed to prevent contamination.

<Construction of Cell Structure>

A 20-layer cell structure formed from NHDFs and HUVECs (NHDFs: $2\times10^6$ cells/well; HUVECs: 1.5% of the total number of NHDFs) and having a vascular network structure was constructed in the same manner as the cell structure constructed in Example 1.

In addition, by changing the content of HUVECs in the cell structure with respect to the total number of NHDFs (hereinafter sometimes referred to as HUVEC content) so as to change the ratio of vascular endothelial cells in the 3D tissue, cell structures (20 layers) having a HUVEC content of 0%, 0.5%, 5.0%, and 15% were constructed.

In other words, in this example, five types of cell structures (20 layers) with a HUVEC content of 0%, 0.5%, 1.5%, 5.0%, and 15% were constructed.

<Seeding of Cancer Cells>

JC406-1-TT cells derived from a patient tumor tissue were suspended in an appropriate amount of D-MEM medium (with 10% FBS) and seeded on the top surface of a cell structure (HUVEC content: 1.5%) constructed in a 24-well Transwell cell culture insert. Thereafter, they were cultured in D-MEM medium (with 10% FBS) for 14 days while appropriately replacing the medium.

Further, in a similar manner, the JC406-1-TT cells derived from a patient tumor tissue were seeded on the top surface of the cell structure with a HUVEC content of 0%, 0.5%, 5.0%, and 15%, and were cultured in D-MEM medium (with 10% FBS) for 14 days while appropriately replacing the medium.

It should be noted that the number of cells derived from the patient tumor tissue and seeded on the cell structure was $1\times10^4$ cells/well.

<Enzyme Treatment and Measurement of EpCAM Positive Cells>

In the same manner as in Examples 4 to 6, after removing the medium from the cultured cell structure, the cell structure was washed with PBS and treated with an enzyme included in the Tumor Dissociation Kit (manufactured by Miltenyi Biotec) to disperse the cells constituting the cell structure. Thereafter, the enzyme-treated product was subjected to immunofluorescence staining with an anti-EpCAM antibody, and the ratio of EpCAM positive cells was measured using an automated cell counter with a fluorescence filter.

For each cell structure, the relative number of cells after culture was calculated as the growth rate of cells (JC406-1-TT cells) when the number of cells (the number of JC406-1-TT cells) (seeded on the top surface of the cell structure) before the start of culture was taken as 1.

Figure 15:
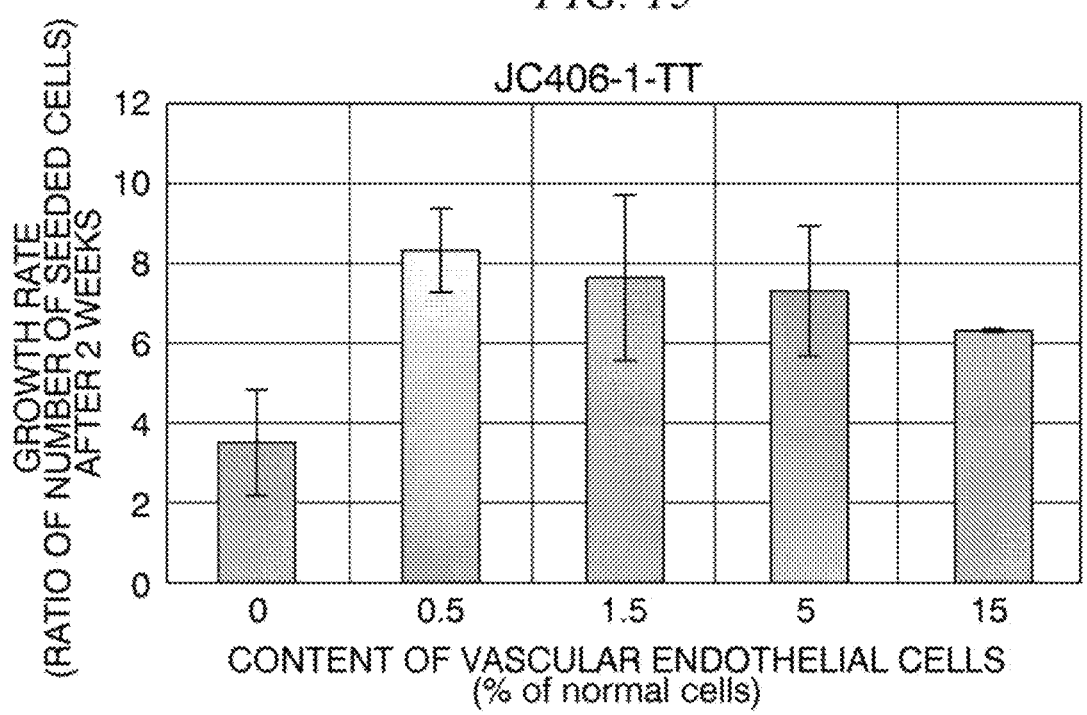
FIG. 15 is a diagram showing results of measuring the growth rate (ratio of number of seeded cells) after 14 days in a sample obtained by seeding JC406-1-TT cells derived from a patient tumor tissue (primary lesion of colorectal cancer) on the top surface of a cell structure containing stromal cells and culturing for 14 days, when the content of vascular endothelial cells in the constituting cell structure is changed in Example 7.

FIG. 15 shows the result of calculating the growth rate of a sample obtained by seeding JC406-1-TT cells derived from a patient tumor tissue on the top surface of a cell structure containing stromal cells and in which the HUVEC content was changed between 0 and 15%, and culturing for 14 days using D-MEM medium.

In other words, FIG. 15 is a diagram showing results of measuring the growth rate (ratio of number of seeded cells) after 14 days in a sample obtained by seeding JC406-1-TT cells derived from a patient tumor tissue (primary lesion of colorectal cancer) on the top surface of a cell structure containing stromal cells and culturing for 14 days, when the content of vascular endothelial cells in the constituting cell structure is changed in Example 7.

As shown in FIG. 15, according to this example, it became clear that cancer cells showed a higher growth rate in a tissue containing vascular endothelial cells such as HUVECs than in a cell structure (3D tissue) formed only from fibroblasts such as NHDFs.

That is, according to this example, when the cell structure includes vascular endothelial cells, favorable results are obtained from the viewpoint of cancer cell proliferation, regardless of the ratio of vascular endothelial cells (HUVECs) in the cell structure.

In addition, according to this example, when the ratio of vascular endothelial cells to fibroblasts was in the range of 0.5% to 5.0%, the growth rate of cancer cells particularly tended to increase.

According to this example, from the viewpoint of obtaining even more cancer cells, it was shown that it is possibly preferable to form a vascular network structure by including vascular endothelial cells in the cell structure.

Although the embodiments of the present invention have been described above, the configurations, combinations thereof, and the like in the embodiments are merely examples, and additions, omissions, substitutions, and other modifications of the configurations are possible without departing from the spirit of the present invention. Further, the present invention is not limited by the embodiments.

What is claimed is:

1. A primary culture method comprising:
seeding first cells on and in direct contact with seconds cells of a top surface of a cell structure, the cell structure being composed of a single layer of second cells or two or more cell layers of second cells laminated in the thickness direction, the second cells constituting a stroma; and
primary culturing the first cells in vitro after seeding, the primary culturing being performed while the first cells are on and in direct contact with the top surface of the cell structure,
wherein the first cells are cancer cells recovered from the tissue collected from a living body,
wherein the second cells are one or more members selected from the group consisting of fibroblasts, pericytes, endothelial cells, and immune cells, and
wherein the cell structure includes a vascular network structure.

2. The primary culture method according to claim 1, wherein the endothelial cells are one or more members selected from the group consisting of vascular endothelial cells and lymphatic endothelial cells.

3. The primary culture method according to claim 2, wherein a thickness of the cell structure is 5 µm or more.

4. The primary culture method according to claim 2, wherein the tissue collected from the living body comprises a tumor tissue.

5. The primary culture method according to claim 4, further comprising:
fragmenting the tissue collected from the living body; and
sorting the first cells which are cancer cells from an obtained fragmented material before primary culturing the first cells.

6. The primary culture method according to claim 5, wherein sorting the first cells from the fragmented material is performed by one or more techniques selected from the group consisting of flow cytometry, magnetic separation, dielectrophoresis, size fractionation, and density gradient fractionation.

7. The primary culture method according to claim 4, further comprising forming the cell structure by a method comprising:
obtaining a mixture by mixing the second cells constituting the stroma, a strong polyelectrolyte, and an extracellular matrix component in a cationic buffer solution;
seeding the mixture in a cell culture vessel; and
obtaining the cell structure in which the second cells constituting the stroma are laminated in multiple layers in the cell culture vessel after seeding the mixture.

8. The primary culture method according to claim 1, wherein a thickness of the cell structure is 5 µm or more.

9. The primary culture method according to claim 1, wherein a thickness of the cell structure is 150 µm or more.

10. The primary culture method according to claim 1, wherein the tissue collected from the living body comprises a tumor tissue.

11. The primary culture method according to claim 10, further comprising:
fragmenting the tissue collected from the living body; and
sorting the first cells which are cancer cells from an obtained fragmented material before primary culturing the first cells.

12. The primary culture method according to claim 11, wherein sorting the first cells from the fragmented material is performed by one or more techniques selected from the group consisting of flow cytometry, magnetic separation, dielectrophoresis, size fractionation, and density gradient fractionation.

13. The primary culture method according to claim 1, further comprising forming the cell structure by a method comprising:
obtaining a mixture by mixing the second cells constituting the stroma, a strong polyelectrolyte, and an extracellular matrix component in a cationic buffer solution;
seeding the mixture in a cell culture vessel; and
obtaining the cell structure in which the second cells constituting the stroma are laminated in multiple layers in the cell culture vessel after seeding the mixture.

14. The primary culture method according to claim 1, wherein the first cells includes cancer cells collected from a fragmented material of the tissue collected from a living body or cancer cells collected from an enzyme-treated product of the tissue collected from the living body.

15. A primary cultured cell-containing cell structure, comprising:
a cell structure comprising second cells constituting a stroma, the cell structure being composed of a single layer of second cells or two or more cell layers of second cells laminated in a thickness direction; and
a cell layer formed from first cells on and in direct contact with second cells of a top surface of the cell structure,
wherein the first cells are cancer cells recovered from the tissue collected from a living body,
wherein the second cells are one or more members selected from the group consisting of fibroblasts, pericytes, endothelial cells, and immune cells, and
wherein the cell structure includes a vascular network structure.

* * * * *

UNITED STATES PATENT AND TRADEMARK OFFICE
CERTIFICATE OF CORRECTION

| | | |
|---|---|---|
| PATENT NO. | : 11,781,115 B2 | Page 1 of 1 |
| APPLICATION NO. | : 16/782579 | |
| DATED | : October 10, 2023 | |
| INVENTOR(S) | : Yuki Takahashi et al. | |

It is certified that error appears in the above-identified patent and that said Letters Patent is hereby corrected as shown below:

On the Title Page

Column 1, Line 1, Item (73), First Assignee, delete "Yo" and insert --Tokyo--.

Signed and Sealed this
First Day of October, 2024

*Katherine Kelly Vidal*

Katherine Kelly Vidal
*Director of the United States Patent and Trademark Office*